US008691950B2

(12) United States Patent
Zheng et al.

(10) Patent No.: US 8,691,950 B2
(45) Date of Patent: Apr. 8, 2014

(54) ***TREPONEMA PALLIDUM* TRIPLET ANTIGEN**

(75) Inventors: Jian Zheng, Raritan, NJ (US); Renee Yura, Bridgewater, NJ (US); Jianping Yang, Tyler, TX (US)

(73) Assignee: Orth-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 13/350,235

(22) Filed: Jan. 13, 2012

(65) Prior Publication Data

US 2012/0237956 A1 Sep. 20, 2012

Related U.S. Application Data

(60) Provisional application No. 61/432,570, filed on Jan. 13, 2011.

(51) Int. Cl.
*C12P 21/02* (2006.01)
*G01N 33/571* (2006.01)
*C07K 14/20* (2006.01)

(52) U.S. Cl.
USPC .......................................... 530/350; 435/7.32

(58) Field of Classification Search
None
See application file for complete search history.

(56) References Cited

U.S. PATENT DOCUMENTS

| | | | | |
|---|---|---|---|---|
| 4,514,498 | A | 4/1985 | Kettman et al. | |
| 4,740,467 | A | 4/1988 | Kettman et al. | |
| 4,868,118 | A | 9/1989 | Norgard | |
| 5,330,893 | A | 7/1994 | Gilbert et al. | |
| 5,342,921 | A | 8/1994 | Cousens et al. | |
| 5,350,842 | A | 9/1994 | Norgard | |
| 5,578,456 | A | 11/1996 | Fujimura et al. | |
| 5,681,934 | A | 10/1997 | Norgard | |
| 6,248,331 | B1 | 6/2001 | Ise et al. | |
| 6,479,248 | B1 | 11/2002 | Krell et al. | |
| 6,794,155 | B2 | 9/2004 | Ise et al. | |
| 2001/0002311 | A1 | 5/2001 | Ise et al. | |
| 2002/0045278 | A1* | 4/2002 | Saruta et al. | 436/807 |
| 2003/0100103 | A1* | 5/2003 | Saruta et al. | 435/287.2 |
| 2009/0104650 | A1 | 4/2009 | Walton et al. | |

FOREIGN PATENT DOCUMENTS

| | | | |
|---|---|---|---|
| EP | 0984065 | A1 | 3/2000 |
| WO | WO 2006/138324 | A2 | 12/2006 |

OTHER PUBLICATIONS

Akins et al., Lipid Modification of the 17-Kilodalton Membrane Immunogen of *Treponema pallidum* Determines Macrophage Activation as well as Amphiphilicity, Infection and Immunity 61(4):1202-1210 (1993).

Castro et al., Evaluation of an Enzyme Immunoassay Technique for Detection of Antibodies against *Treponema pallidum* Evaluation of an enzyme immunoassay technique for, Journal of Clinical Microbiology 41(1):250-253 (2003).

Hallewell et al., Genetically Engineered Polymers of Human CuZn Superoxide Dismutase, Journal of Biological Chemistry 264(9):5260-5268 (1989).

Morse, Stephen A., Advances in diagnostic tests for bacterial STDs, Salud Pública Méx 45 Supl 5:S698-S708 (2003) English Abstract.

Norgard et al., Cloning and Expression of the Major 47-Kilodalton Surface Immunogen of *Treponema pallidum* in *Escherichia coli*, Infection and Immunity 54(2):500-506 (1986).

Purcell et al. Molecular Cloning and Characterization of the 15-Kilodalton Major Immunogen of *Treponema pallidum*, Infection and Immunity 57(12):3708-3714 (1989).

Schmidt et al., Comparative Evaluation of Nine Different Enzyme-Linked Immunosorbent Assays for Determination of Antibodies against *Treponema pallidum* in Patients with Primary Syphilis, Journal of Clinical Microbiology 38(3):1279-1282 (2000).

* cited by examiner

*Primary Examiner* — Robert A Zeman
(74) *Attorney, Agent, or Firm* — Susan J. Timian

(57) ABSTRACT

A *Treponema pallidum* triplet antigen construct is disclosed which includes three *Treponema pallidum* antigens (TP15, TP17, and TP47), as well as a ten amino acid leader sequence (tag 261) and human copper zinc superoxide dismutase (hSOD). This construct is optimized for in vitro diagnosis of syphilis infection. Plasmids containing DNA encoding the triplet antigen, host cells, production methods, detection methods, and kits are also disclosed.

8 Claims, 9 Drawing Sheets

SEQUENCE LISTING

<160> NUMBER OF SEQ ID NOS: 33

<210> SEQ ID NO 1
<211> LENGTH: 2544
<212> TYPE: DNA

-continued

<213> ORGANISM: Treponema pallidum

<400> SEQUENCE: 1

```
atgcgtggat ctgctgtgcc gcctcaacag tgggccttgt ctggatccag cttttctagt      60
attccgaacg gcacctatcg tgcgacgtac caggatttcg atgaaaatgg ttggaaagat     120
tttctggaag tgaccttcga tggcggtaaa atggttcagg tggtttatga ttaccagcat     180
aaagaaggcc gctttaaaag ccaggatgcc gattatcacc gtgtgatgta cgcatctagt     240
ggtatcggtc cagaaaaagc gttccgcgaa ctggccgatg cactgctgga aaaaggtaac     300
ccggaaatgg ttgatgtggt tacgggcgcg accgtgagct ctcagagttt tcgtcgcctg     360
ggtcgtgccc tgctgcagag cgcacgccgt ggcgaaaaag aagccattat ctctcgcggt     420
agatccgtga gctgcaccac ggtttgtccg catgcgggca aagccaaagc agaaaaagtg     480
gaatgcgcgc tgaaaggtgg catttttcgt ggtaccctgc cggccgcaga ttgtccgggc     540
atcgatacga ccgttacgtt caacgcggat ggtaccgccc agaaagtgga actggcactg     600
gaaaagaaaa gcgcgccgag tccgctgacg tatcgcggca cctggatggt tcgtgaagat     660
ggtattgtgg aactgagcct ggtttctagt gaacagagca aagccccgca cgaaaaagaa     720
ctgtacgaac tgatcgattc taatagcgtg cgctatatgg gcgcaccggg tgcgggcaaa     780
ccgagcaaag aaatggcccc gttttacgtt ctgaagaaaa ccaagaaagg cccgagatcc     840
ggcagctctc atcacgaaac ccattatggt tacgcgacgc tgagttatgc cgattactgg     900
gcaggcgaac tgggtcagag ccgtgatgtg ctgctggcgg gcaacgccga agcagatcgc     960
gcgggtgatc tggatgccgg catgtttgat gcagtttctc gtgcgaccca cggtcatggc    1020
gccttccgcc agcagtttca gtatgcagtg gaagttctgg gtgaaaaagt gctgagtaaa    1080
caggaaacgg aagatagccg tggccgcaaa aaatgggaat acgaaaccga tccgtctgtt    1140
acgaaaatgg tgcgtgcgag tgccagcttc caggatctgg gtgaagatgg cgaaattaaa    1200
tttgaagcag ttgaaggtgc ggtggccctg gcagatcgcg cgtctagttt catggttgat    1260
agcgaagaat ataaaatcac caatgtgaaa gttcacggca tgaaatttgt gccggttgcc    1320
gtgccgcatg aactgaaagg tattgcaaaa gaaaaattcc actttgttga agattctcgt    1380
gtgacggaaa acaccaatgg cctgaaaacg atgctgaccg aagatagttt cagcgcgcgc    1440
aaagtttcta gtatggaaag cccgcatgat ctggtggttg atacggtggg taccggctac    1500
cactctcgtt ttggtagtga tgccgaagca agcgttatgc tgaaacgcgc ggatggctct    1560
gaactgagtc atcgtgaatt tatcgattat gtgatgaact ttaatacggt tcgctacgat    1620
tattacggtg atgatgccag ctataccaac ctgatggcat cttacggcac gaaacacagt    1680
gcggattctt ggtggaaaac cggtcgtgtg ccgcgcattt cttgcggcat caattatggt    1740
ttcgatcgtt ttaaaggcag cggtccgggc tactatcgcc tgacgctgat tgccaacggt    1800
taccgtgatg ttgtggcaga tgttcgcttc ctgccgaaat atgaaggcaa tatcgatatt    1860
ggtctgaaag gcaaagtgct gaccatcggt ggcgcggatg ccgaaaccct gatggatgca    1920
gccgttgatg tgtttgcgga tggtcagccg aaactggtta gcgatcaggc cgtgagcctg    1980
ggccagaacg ttctgagcgc ggatttcacc ccgggtaccg aatataccgt ggaagttcgt    2040
tttaaagaat ttggcagcgt gcgcgcgaaa gtggtggcgc agctcgcgac caaagccgtc    2100
agcgtgctga aaggcgatgg tccggttcag ggtatcatca acttcgaaca aaaagaaagc    2160
aatggtccgg ttaaagtctg gggctctatt aaaggtctga cggaaggcct gcatggtttt    2220
catgtccacg aatttggcga caacaccgca ggttgcacga gtgctggccc gcatttcaat    2280
```

ccgctgtcac gtaaacacgg cggtccgaaa gatgaagaac gccacgtcgg cgacctgggt 2340
aacgtgaccg cagataaaga cggtgtggct gatgttagta ttgaagactc cgtgatcagc 2400
ctgtctggtg atcattccat tatcggccgt accctggtgg tgcacgaaaa agcagatgac 2460
ctgggcaaag gcggtaacga agaatcaacc aaaacgggta atgcaggttc gcgtctggca 2520
tgtggcgtta ttggtatcgc ccag 2544

<210> SEQ ID NO 2
<211> LENGTH: 2538
<212> TYPE: DNA
<213> ORGANISM: Treponema pallidum

<400> SEQUENCE: 2
atgcgtggat ctgctgtgcc gcctcaacag tgggccttgt ctggatccag cttttctagt 60
attccgaacg gcacctatcg tgcgacgtac caggatttcg atgaaaatgg ttggaaagat 120
tttctggaag tgaccttcga tggcggtaaa atggttcagg tggtttatga ttaccagcat 180
aaagaaggcc gctttaaaag ccaggatgcc gattatcacc gtgtgatgta cgcatctagt 240
ggtatcggtc cagaaaaagc gttccgcgaa ctggccgatg cactgctgga aaaaggtaac 300
ccggaaatgg ttgatgtggt tacgggcgcg accgtgagct ctcagagttt tcgtcgcctg 360
ggtcgtgccc tgctgcagag cgcacgccgt ggcgaaaaag aagccattat ctctcgcggt 420
agatccggca gctctcatca cgaaacccat tatggttacg cgacgctgag ttatgccgat 480
tactgggcag gcgaactggg tcagagccgt gatgtgctgc tggcgggcaa cgccgaagca 540
gatcgcgcgg gtgatctgga tgccggcatg tttgatgcag tttctcgtgc gacccacggt 600
catggcgcct tccgccagca gtttcagtat gcagtggaag ttctgggtga aaaagtgctg 660
agtaaacagg aaacggaaga tagccgtggc cgcaaaaaat gggaatacga aaccgatccg 720
tctgttacga aaatggtgcg tgcgagtgcc agcttccagg atctgggtga agatggcgaa 780
attaaatttg aagcagttga aggtgcggtg gccctggcag atcgcgcgtc tagtttcatg 840
gttgatagcg aagaatataa aatcaccaat gtgaaagttc acggcatgaa atttgtgccg 900
gttgccgtgc cgcatgaact gaaaggtatt gcaaaagaaa aattccactt tgttgaagat 960
tctcgtgtga cggaaaacac caatggcctg aaaacgatgc tgaccgaaga tagtttcagc 1020
gcgcgcaaag tttctagtat ggaaagcccg catgatctgg tggttgatac ggtgggtacc 1080
ggctaccact ctcgttttgg tagtgatgcc gaagcaagcg ttatgctgaa acgcgcggat 1140
ggctctgaac tgagtcatcg tgaatttatc gattatgtga tgaactttaa tacggttcgc 1200
tacgattatt acggtgatga tgccagctat accaacctga tggcatctta cggcacgaaa 1260
cacagtgcgg attcttggtg gaaaaccggt cgtgtgccgc gcatttcttg cggcatcaat 1320
tatggtttcg atcgttttaa aggcagcggt ccgggctact atcgcctgac gctgattgcc 1380
aacggttacc gtgatgttgt ggcagatgtt cgcttcctgc cgaaatatga aggcaatatc 1440
gatattggtc tgaaaggcaa agtgctgacc atcggtggcg cggatgccga aaccctgatg 1500
gatgcagccg ttgatgtgtt tgcggatggt cagccgaaac tggttagcga tcaggccgtg 1560
agcctgggcc agaacgttct gagcgcggat ttcacccggg gtaccgaata taccgtggaa 1620
gttcgtttta aagaatttgg cagcgtgcgc gcgaaagtgg tggcgcaggg gcccgtgagc 1680
tgcaccacgg tttgtccgca tgcgggcaaa gccaaagcag aaaaagtgga atgcgcgctg 1740
aaaggtggca tttttcgtgg taccctgccg gccgcagatt gtccgggcat cgatacgacc 1800
gttacgttca acgcggatgg taccgcccag aaagtggaac tggcactgga aaagaaaagc 1860

-continued gcgccgagtc cgctgacgta tcgcggcacc tggatggttc gtgaagatgg tattgtggaa 1920
ctgagcctgg tttctagtga acagagcaaa gccccgcacg aaaaagaact gtacgaactg 1980
atcgattcta atagcgtgcg ctatatgggc gcaccgggtg cgggcaaacc gagcaaagaa 2040
atggccccgt tttacgttct gaagaaaacc aagaaactcg cgaccaaagc cgtcagcgtg 2100
ctgaaaggcg atggtccggt tcagggtatc atcaacttcg aacaaaaaga aagcaatggt 2160
ccggttaaag tctggggctc tattaaaggt ctgacggaag gcctgcatgg ttttcatgtc 2220
cacgaatttg gcgacaacac cgcaggttgc acgagtgctg gcccgcattt caatccgctg 2280
tcacgtaaac acggcggtcc gaaagatgaa gaacgccacg tcggcgacct gggtaacgtg 2340
accgcagata aagacggtgt ggctgatgtt agtattgaag actccgtgat cagcctgtct 2400
ggtgatcatt ccattatcgg ccgtaccctg gtggtgcacg aaaaagcaga tgacctgggc 2460
aaaggcggta acgaagaatc aaccaaaacg ggtaatgcag gttcgcgtct ggcatgtggc 2520
gttattggta tcgcccag 2538

<210> SEQ ID NO 3
<211> LENGTH: 2547
<212> TYPE: DNA
<213> ORGANISM: Treponema pallidum

<400> SEQUENCE: 3
atgcgtggat ctgctgtgcc gcctcaacag tgggccttgt ctggatccgt gagctgcacc 60
acggtttgtc cgcatgcggg caaagccaaa gcagaaaaag tggaatgcgc gctgaaaggt 120
ggcatttttc gtggtaccct gccggccgca gattgtccgg gcatcgatac gaccgttacg 180
ttcaacgcgg atggtaccgc ccagaaagtg gaactggcac tggaaaagaa aagcgcgccg 240
agtccgctga cgtatcgcgg cacctggatg gttcgtgaag atggtattgt ggaactgagc 300
ctggtttcta gtgaacagag caaagccccg cacgaaaaag aactgtacga actgatcgat 360
tctaatagcg tgcgctacat gggcgcaccg ggtgcgggca aaccgagcaa agaaatggcc 420
ccgttttacg ttctgaagaa aaccaagaaa ggcccgagat ccagcttttc tagtattccg 480
aacggcacct atcgtgcgac gtaccaggat ttcgatgaaa atggttggaa agattttctg 540
gaagtgacct tcgatggcgg taaaatggtt caggtggttt atgattacca gcataaagaa 600
ggccgcttta aaagccagga tgccgattat caccgtgtga tgtacgcatc tagtggtatc 660
ggtccagaaa aagcgttccg cgaactggcc gatgcactgc tggaaaaagg taacccggaa 720
atggttgatg tggttacggg cgcgaccgtg agctctcaga gttttcgtcg cctgggtcgt 780
gccctgctgc agagcgcacg ccgtggcgaa aaagaagcca ttatctctcg cggcccgaga 840
tccggcagct ctcatcacga aacccattat ggttacgcga cgctgagtta tgccgattac 900
tgggcaggcg aactgggtca gagccgtgat gtgctgctgg cgggcaacgc cgaagcagat 960
cgcgcgggtg atctggatgc cggcatgttt gatgcagttt ctcgtgcgac ccacggtcat 1020
ggcgccttcc gccagcagtt tcagtatgca gtggaagttc tgggtgaaaa agtgctgagt 1080
aaacaggaaa cggaagatag ccgtggccgc aaaaaatggg aatacgaaac cgatccgtct 1140
gttacgaaaa tggtgcgtgc gagtgccagc ttccaggatc tgggtgaaga tggcgaaatt 1200
aaatttgaag cagttgaagg tgcggtggcc ctggcagatc gcgcgtctag tttcatggtt 1260
gatagcgaag aatataaaat caccaatgtg aaagttcacg gcatgaaatt tgtgccggtt 1320
gccgtgccgc atgaactgaa aggtattgca aaagaaaaat tccactttgt tgaagattct 1380
cgtgtgacgg aaaacaccaa tggcctgaaa acgatgctga ccgaagatag tttcagcgcg 1440

-continued

```
cgcaaagttt ctagtatgga aagcccgcat gatctggtgg ttgatacggt gggtaccggc   1500

taccactctc gttttggtag tgatgccgaa gcaagcgtta tgctgaaacg cgcggatggc   1560

tctgaactga gtcatcgtga atttatcgat tatgtgatga actttaatac ggttcgctac   1620

gattattacg gtgatgatgc cagctatacc aacctgatgg catcttacgg cacgaaacac   1680

agtgcggatt cttggtggaa aaccggtcgt gtgccgcgca tttcttgcgg catcaattat   1740

ggtttcgatc gttttaaagg cagcggtccg ggctactatc gcctgacgct gattgccaac   1800

ggttaccgtg atgttgtggc agatgttcgc ttcctgccga aatatgaagg caatatcgat   1860

attggtctga aaggcaaagt gctgaccatc ggtggcgcgg atgccgaaac cctgatggat   1920

gcagccgttg atgtgtttgc ggatggtcag ccgaaactgg ttagcgatca ggccgtgagc   1980

ctgggccaga acgttctgag cgcggatttc accccgggta ccgaatatac cgtggaagtt   2040

cgttttaaag aatttggcag cgtgcgcgcg aaagtggtgg cgcagctcgc gaccaaagcc   2100

gtcagcgtgc tgaaaggcga tggtccggtt cagggtatca tcaacttcga acaaaaagaa   2160

agcaatggtc cggttaaagt ctggggctct attaaaggtc tgacggaagg cctgcatggt   2220

tttcatgtcc acgaatttgg cgacaacacc gcaggttgca cgagtgctgg cccgcatttc   2280

aatccgctgt cacgtaaaca cggcggtccg aaagatgaag aacgccacgt cggcgacctg   2340

ggtaacgtga ccgcagataa agacggtgtg gctgatgtta gtattgaaga ctccgtgatc   2400

agcctgtctg gtgatcattc cattatcggc cgtaccctgg tggtgcacga aaaagcagat   2460

gacctgggca aaggcggtaa cgaagaatca accaaaacgg gtaatgcagg ttcgcgtctg   2520

gcatgtggcg ttattggtat cgcccag                                       2547
```

<210> SEQ ID NO 4
<211> LENGTH: 2541
<212> TYPE: DNA
<213> ORGANISM: Treponema pallidum

<400> SEQUENCE: 4

```
atgcgtggat ctgctgtgcc gcctcaacag tgggccttgt ctggatccgt gagctgcacc     60

acggtttgtc cgcatgcggg caaagccaaa gcagaaaaag tggaatgcgc gctgaaaggt    120

ggcatttttc gtggtaccct gccggccgca gattgtccgg gcatcgatac gaccgttacg    180

ttcaacgcgg atggtaccgc ccagaaagtg gaactggcac tggaaaagaa aagcgcgccg    240

agtccgctga cgtatcgcgg cacctggatg gttcgtgaag atggtattgt ggaactgagc    300

ctggtttcta gtgaacagag caaagccccg cacgaaaaag aactgtacga actgatcgat    360

tctaatagcg tgcgctatat gggcgcaccg ggtgcgggca aaccgagcaa agaaatggcc    420

ccgttttacg ttctgaagaa aaccaagaaa ggcccgagat ccggcagctc tcatcacgaa    480

acccattatg gttacgcgac gctgagttat gccgattact gggcaggcga actgggtcag    540

agccgtgatg tgctgctggc gggcaacgcc gaagcagatc gcgcgggtga tctggatgcc    600

ggcatgtttg atgcagtttc tcgtgcgacc cacggtcatg gcgccttccg ccagcagttt    660

cagtatgcag tggaagttct gggtgaaaaa gtgctgagta aacaggaaac ggaagatagc    720

cgtggccgca aaaaatggga atacgaaacc gatccgtctg ttacgaaaat ggtgcgtgcg    780

agtgccagct tccaggatct gggtgaagat ggcgaaatta aatttgaagc agttgaaggt    840

gcggtggccc tggcagatcg cgcgtctagt ttcatggttg atagcgaaga atataaaatc    900

accaatgtga aagttcacgg catgaaattt gtgccggttg ccgtgccgca tgaactgaaa    960

ggtattgcaa aagaaaaatt ccactttgtt gaagattctc gtgtgacgga aaacaccaat   1020
```

-continued

```
ggcctgaaaa cgatgctgac cgaagatagt ttcagcgcgc gcaaagtttc tagtatggaa   1080

agcccgcatg atctggtggt tgatacggtg ggtaccggct accactctcg ttttggtagt   1140

gatgccgaag caagcgttat gctgaaacgc gcggatggct ctgaactgag tcatcgtgaa   1200

tttatcgatt atgtgatgaa ctttaatacg gttcgctacg attattacgg tgatgatgcc   1260

agctatacca acctgatggc atcttacggc acgaaacaca gtgcggattc ttggtggaaa   1320

accggtcgtg tgccgcgcat ttcttgcggc atcaattatg gtttcgatcg ttttaaaggc   1380

agcggtccgg gctactatcg cctgacgctg attgccaacg gttaccgtga tgttgtggca   1440

gatgttcgct tcctgccgaa atatgaaggc aatatcgata ttggtctgaa aggcaaagtg   1500

ctgaccatcg gtggcgcgga tgccgaaacc ctgatggatg cagccgttga tgtgtttgcg   1560

gatggtcagc cgaaactggt tagcgatcag gccgtgagcc tgggccagaa cgttctgagc   1620

gcggatttca ccccgggtac cgaatatacc gtggaagttc gttttaaaga atttggcagc   1680

gtgcgcgcga aagtggtggc gcaggggccc agcttttcta gtattccgaa cggcacctat   1740

cgtgcgacgt accaggattt cgatgaaaat ggttggaaag attttctgga agtgaccttc   1800

gatggcggta aaatggttca ggtggtttat gattaccagc ataaagaagg ccgctttaaa   1860

agccaggatg ccgattatca ccgtgtgatg tacgcatcta gtggtatcgg tccagaaaaa   1920

gcgttccgcg aactggccga tgcactgctg gaaaaaggta acccggaaat ggttgatgtg   1980

gttacgggcg cgaccgtgag ctctcagagt tttcgtcgcc tgggtcgtgc cctgctgcag   2040

agcgcacgcc gtggcgaaaa agaagccatt atctctcgcc tcgcgaccaa agccgtcagc   2100

gtgctgaaag gcgatggtcc ggttcagggt atcatcaact tcgaacaaaa agaaagcaat   2160

ggtccggtta aagtctgggg ctctattaaa ggtctgacgg aaggcctgca tggttttcat   2220

gtccacgaat ttggcgacaa caccgcaggt tgcacgagtg ctggcccgca tttcaatccg   2280

ctgtcacgta aacacggcgg tccgaaagat gaagaacgcc acgtcggcga cctgggtaac   2340

gtgaccgcag ataaagacgg tgtggctgat gttagtattg aagactccgt gatcagcctg   2400

tctggtgatc attccattat cggccgtacc ctggtggtgc acgaaaaagc agatgacctg   2460

ggcaaaggcg gtaacgaaga atcaaccaaa acgggtaatg caggttcgcg tctggcatgt   2520

ggcgttattg gtatcgccca g                                              2541
```

<210> SEQ ID NO 5
<211> LENGTH: 2541
<212> TYPE: DNA
<213> ORGANISM: Treponema pallidum

<400> SEQUENCE: 5

```
atgcgtggat ctgctgtgcc gcctcaacag tgggccttgt ctggatccgg cagctctcat     60

cacgaaaccc attatggtta cgcgacgctg agttatgccg attactgggc aggcgaactg    120

ggtcagagcc gtgatgtgct gctggcgggc aacgccgaag cagatcgcgc gggtgatctg    180

gatgccggca tgtttgatgc agtttctcgt gcgacccacg gtcatggcgc cttccgccag    240

cagtttcagt atgcagtgga agttctgggt gaaaaagtgc tgagtaaaca ggaaacggaa    300

gatagccgtg gccgcaaaaa atgggaatac gaaaccgatc cgtctgttac gaaaatggtg    360

cgtgcgagtg ccagcttcca ggatctgggt gaagatggcg aaattaaatt tgaagcagtt    420

gaaggtgcgg tggccctggc agatcgcgcg tctagtttca tggttgatag cgaagaatat    480

aaaatcacca atgtgaaagt tcacggcatg aaatttgtgc cggttgccgt gccgcatgaa    540

ctgaaaggta ttgcaaaaga aaaattccac tttgttgaag attctcgtgt gacggaaaac    600
```

-continued

```
accaatggcc tgaaaacgat gctgaccgaa gatagtttca gcgcgcgcaa agtttctagt    660

atggaaagcc cgcatgatct ggtggttgat acggtgggta ccggctacca ctctcgtttt    720

ggtagtgatg ccgaagcaag cgttatgctg aaacgcgcgg atggctctga actgagtcat    780

cgtgaattta tcgattatgt gatgaacttt aatacggttc gctacgatta ttacggtgat    840

gatgccagct ataccaacct gatggcatct tacggcacga aacacagtgc ggattcttgg    900

tggaaaaccg gtcgtgtgcc gcgcatttct tgcggcatca attatggttt cgatcggttt    960

aaaggcagcg gtccgggcta ctatcgcctg acgctgattg ccaacggtta ccgtgatgtt   1020

gtggcagatg ttcgcttcct gccgaaatat gaaggcaata tcgatattgg tctgaaaggc   1080

aaagtgctga ccatcggtgg cgcggatgcc gaaaccctga tggatgcagc cgttgatgtg   1140

tttgcggatg gtcagccgaa actggttagc gatcaggccg tgagcctggg ccagaacgtt   1200

ctgagcgcgg atttcacccc gggtaccgaa tataccgtgg aagttcgttt taaagaattt   1260

ggcagcgtgc gcgcgaaagt ggtggcgcag ggtccaagat ccagcttttc tagtattccg   1320

aacggcacct atcgtgcgac gtaccaggat ttcgatgaaa atggttggaa agattttctg   1380

gaagtgacct tcgatggcgg taaaatggtt caggtggttt atgattacca gcataaagaa   1440

ggccgcttta aaagccagga tgccgattat caccgtgtga tgtacgcatc tagtggtatc   1500

ggtccagaaa aagcgttccg cgaactggcc gatgcactgc tggaaaaagg taacccggaa   1560

atggttgatg tggttacggg cgcgaccgtg agctctcaga gttttcgtcg cctgggtcgt   1620

gccctgctgc agagcgcacg ccgtggcgaa aaagaagcca ttatctctcg cgggcccgtg   1680

agctgcacca cggtttgtcc gcatgcgggc aaagccaaag cagaaaaagt ggaatgcgcg   1740

ctgaaaggtg gcatttttcg tggtaccctg ccggccgcag attgtccggg catcgatacg   1800

accgttacgt tcaacgcgga tggtaccgcc cagaaagtgg aactggcact ggaaaagaaa   1860

agcgcgccga gtccgctgac gtatcgcggc acctggatgg ttcgtgaaga tggtattgtg   1920

gaactgagcc tggtttctag tgaacagagc aaagccccgc acgaaaaaga actgtacgaa   1980

ctgatcgatt ctaatagcgt gcgctatatg ggcgcaccgg gtgcgggcaa accgagcaaa   2040

gaaatggccc cgttttacgt tctgaagaaa accaagaaac tcgcgaccaa agccgtcagc   2100

gtgctgaaag gcgatggtcc ggttcagggt atcatcaact tcgaacaaaa agaaagcaat   2160

ggtccggtta aagtctgggg ctctattaaa ggtctgacgg aaggcctgca tggttttcat   2220

gtccacgaat ttggcgacaa caccgcaggt tgcacgagtg ctggcccgca tttcaatccg   2280

ctgtcacgta aacacggcgg tccgaaagat gaagaacgcc acgtcggcga cctgggtaac   2340

gtgaccgcag ataaagacgg tgtggctgat gttagtattg aagactccgt gatcagcctg   2400

tctggtgatc attccattat cggccgtacc ctggtggtgc acgaaaaagc agatgacctg   2460

ggcaaaggcg gtaacgaaga atcaaccaaa acgggtaatg caggttcgcg tctggcatgt   2520

ggcgttattg gtatcgccca g                                             2541
```

<210> SEQ ID NO 6
<211> LENGTH: 2547
<212> TYPE: DNA
<213> ORGANISM: Treponema pallidum

<400> SEQUENCE: 6

```
atgcgtggat ctgctgtgcc gcctcaacag tgggccttgt ctggatccgg cagctctcat     60

cacgaaaccc attatggtta cgcgacgctg agttatgccg attactgggc aggcgaactg    120

ggtcagagcc gtgatgtgct gctggcgggc aacgccgaag cagatcgcgc gggtgatctg    180
```

-continued

```
gatgccggca tgtttgatgc agtttctcgt gcgacccacg gtcatggcgc cttccgccag    240
cagtttcagt atgcagtgga agttctgggt gaaaaagtgc tgagtaaaca ggaaacggaa    300
gatagccgtg gccgcaaaaa atgggaatac gaaaccgatc cgtctgttac gaaaatggtg    360
cgtgcgagtg ccagcttcca ggatctgggt gaagatggcg aaattaaatt tgaagcagtt    420
gaaggtgcgg tggccctggc agatcgcgcg tctagtttca tggttgatag cgaagaatat    480
aaaatcacca atgtgaaagt tcacggcatg aaatttgtgc cggttgccgt gccgcatgaa    540
ctgaaaggta ttgcaaaaga aaaattccac tttgttgaag attctcgtgt gacggaaaac    600
accaatggcc tgaaaacgat gctgaccgaa gatagtttca gcgcgcgcaa agtttctagt    660
atggaaagcc cgcatgatct ggtggttgat acggtgggta ccggctacca ctctcgtttt    720
ggtagtgatg ccgaagcaag cgttatgctg aaacgcgcgg atggctctga actgagtcat    780
cgtgaattta tcgattatgt gatgaacttt aatacggttc gctacgatta ttacggtgat    840
gatgccagct ataccaacct gatggcatct tacggcacga aacacagtgc ggattcttgg    900
tggaaaaccg gtcgtgtgcc gcgcatttct tgcggcatca attatggttt cgatcggttt    960
aaaggcagcg gtccgggcta ctatcgcctg acgctgattg ccaacggtta ccgtgatgtt   1020
gtggcagatg ttcgcttcct gccgaaatat gaaggcaata tcgatattgg tctgaaaggc   1080
aaagtgctga ccatcggtgg cgcggatgcc gaaaccctga tggatgcagc cgttgatgtg   1140
tttgcggatg gtcagccgaa actggttagc gatcaggccg tgagcctggg ccagaacgtt   1200
ctgagcgcgg atttcacccc gggtaccgaa tataccgtgg aagttcgttt taaagaattt   1260
ggcagcgtgc gcgcgaaagt ggtggcgcag ggcccgagat ccgtgagctg caccacggtt   1320
tgtccgcatg cgggcaaagc caaagcagaa aaagtggaat gcgcgctgaa aggtggcatt   1380
tttcgtggta ccctgccggc cgcagattgt ccgggcatcg atacgaccgt tacgttcaac   1440
gcggatggta ccgcccagaa agtggaactg gcactggaaa agaaaagcgc gccgagtccg   1500
ctgacgtatc gcggcacctg gatggttcgt gaagatggta ttgtggaact gagcctggtt   1560
tctagtgaac agagcaaagc cccgcacgaa aaagaactgt acgaactgat cgattctaat   1620
agcgtgcgct acatgggcgc accgggtgcg ggcaaaccga gcaaagaaat ggccccgttt   1680
tacgttctga agaaaaccaa gaaaggcccg agatccagct ttctagtat tccgaacggc   1740
acctatcgtg cgacgtacca ggatttcgat gaaaatggtt ggaaagattt tctggaagtg   1800
accttcgatg gcggtaaaat ggttcaggtg gtttatgatt accagcataa agaaggccgc   1860
tttaaaagcc aggatgccga ttatcaccgt gtgatgtacg catctagtgg tatcggtcca   1920
gaaaaagcgt tccgcgaact ggccgatgca ctgctggaaa aaggtaaccc ggaaatggtt   1980
gatgtggtta cgggcgcgac cgtgagctct cagagttttc gtcgcctggg tcgtgccctg   2040
ctgcagagcg cacgccgtgg cgaaaaagaa gccattatct ctcgcctcgc gaccaaagcc   2100
gtcagcgtgc tgaaaggcga tggtccggtt cagggtatca tcaacttcga acaaaaagaa   2160
agcaatggtc cggttaaagt ctggggctct attaaaggtc tgacggaagg cctgcatggt   2220
tttcatgtcc acgaatttgg cgacaacacc gcaggttgca cgagtgctgg cccgcatttc   2280
aatccgctgt cacgtaaaca cggcggtccg aaagatgaag aacgccacgt cggcgacctg   2340
ggtaacgtga ccgcagataa agacggtgtg gctgatgtta gtattgaaga ctccgtgatc   2400
agcctgtctg gtgatcattc cattatcggc cgtaccctgg tggtgcacga aaaagcagat   2460
gacctgggca aaggcggtaa cgaagaatca accaaaacgg gtaatgcagg ttcgcgtctg   2520
gcatgtggcg ttattggtat cgcccag                                        2547
```

<210> SEQ ID NO 7
<211> LENGTH: 848
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(139)
<223> OTHER INFORMATION: Treponema pallidum outer membrane protein TP15
<220> FEATURE:
<221> NAME/KEY: MISC_FEATURE
<222> LOCATION: (143)..(276)
<223> OTHER INFORMATION: Treponema pallidum outer membrane protein TP17
<220> FEATURE:
<221> NAME/KEY: MISC_FEATURE
<222> LOCATION: (281)..(694)
<223> OTHER INFORMATION: Treponema pallidum outer membrane protein TP47
<220> FEATURE:
<221> NAME/KEY: MISC_FEATURE
<222> LOCATION: (696)..(848)
<223> OTHER INFORMATION: human copper zinc superoxide dismutase

<400> SEQUENCE: 7

```
Met Arg Gly Ser Ala Val Pro Pro Gln Gln Trp Ala Leu Ser Gly Ser
1               5                   10                  15

Ser Phe Ser Ser Ile Pro Asn Gly Thr Tyr Arg Ala Thr Tyr Gln Asp
            20                  25                  30

Phe Asp Glu Asn Gly Trp Lys Asp Phe Leu Glu Val Thr Phe Asp Gly
        35                  40                  45

Gly Lys Met Val Gln Val Val Tyr Asp Tyr Gln His Lys Glu Gly Arg
    50                  55                  60

Phe Lys Ser Gln Asp Ala Asp Tyr His Arg Val Met Tyr Ala Ser Ser
65                  70                  75                  80

Gly Ile Gly Pro Glu Lys Ala Phe Arg Glu Leu Ala Asp Ala Leu Leu
                85                  90                  95

Glu Lys Gly Asn Pro Glu Met Val Asp Val Val Thr Gly Ala Thr Val
            100                 105                 110

Ser Ser Gln Ser Phe Arg Arg Leu Gly Arg Ala Leu Leu Gln Ser Ala
        115                 120                 125

Arg Arg Gly Glu Lys Glu Ala Ile Ile Ser Arg Gly Arg Ser Val Ser
    130                 135                 140

Cys Thr Thr Val Cys Pro His Ala Gly Lys Ala Lys Ala Glu Lys Val
145                 150                 155                 160

Glu Cys Ala Leu Lys Gly Gly Ile Phe Arg Gly Thr Leu Pro Ala Ala
                165                 170                 175

Asp Cys Pro Gly Ile Asp Thr Thr Val Thr Phe Asn Ala Asp Gly Thr
            180                 185                 190

Ala Gln Lys Val Glu Leu Ala Leu Glu Lys Lys Ser Ala Pro Ser Pro
        195                 200                 205

Leu Thr Tyr Arg Gly Thr Trp Met Val Arg Glu Asp Gly Ile Val Glu
    210                 215                 220

Leu Ser Leu Val Ser Ser Glu Gln Ser Lys Ala Pro His Glu Lys Glu
225                 230                 235                 240

Leu Tyr Glu Leu Ile Asp Ser Asn Ser Val Arg Tyr Met Gly Ala Pro
                245                 250                 255

Gly Ala Gly Lys Pro Ser Lys Glu Met Ala Pro Phe Tyr Val Leu Lys
            260                 265                 270

Lys Thr Lys Lys Gly Pro Arg Ser Gly Ser Ser His His Glu Thr His
```

-continued

```
        275                 280                 285

Tyr Gly Tyr Ala Thr Leu Ser Tyr Ala Asp Tyr Trp Ala Gly Glu Leu
    290                 295                 300

Gly Gln Ser Arg Asp Val Leu Leu Ala Gly Asn Ala Glu Ala Asp Arg
305                 310                 315                 320

Ala Gly Asp Leu Asp Ala Gly Met Phe Asp Ala Val Ser Arg Ala Thr
                325                 330                 335

His Gly His Gly Ala Phe Arg Gln Gln Phe Gln Tyr Ala Val Glu Val
            340                 345                 350

Leu Gly Glu Lys Val Leu Ser Lys Gln Glu Thr Glu Asp Ser Arg Gly
        355                 360                 365

Arg Lys Lys Trp Glu Tyr Glu Thr Asp Pro Ser Val Thr Lys Met Val
    370                 375                 380

Arg Ala Ser Ala Ser Phe Gln Asp Leu Gly Glu Asp Gly Glu Ile Lys
385                 390                 395                 400

Phe Glu Ala Val Glu Gly Ala Val Ala Leu Ala Asp Arg Ala Ser Ser
                405                 410                 415

Phe Met Val Asp Ser Glu Glu Tyr Lys Ile Thr Asn Val Lys Val His
            420                 425                 430

Gly Met Lys Phe Val Pro Val Ala Val Pro His Glu Leu Lys Gly Ile
        435                 440                 445

Ala Lys Glu Lys Phe His Phe Val Glu Asp Ser Arg Val Thr Glu Asn
    450                 455                 460

Thr Asn Gly Leu Lys Thr Met Leu Thr Glu Asp Ser Phe Ser Ala Arg
465                 470                 475                 480

Lys Val Ser Ser Met Glu Ser Pro His Asp Leu Val Val Asp Thr Val
                485                 490                 495

Gly Thr Gly Tyr His Ser Arg Phe Gly Ser Asp Ala Glu Ala Ser Val
            500                 505                 510

Met Leu Lys Arg Ala Asp Gly Ser Glu Leu Ser His Arg Glu Phe Ile
        515                 520                 525

Asp Tyr Val Met Asn Phe Asn Thr Val Arg Tyr Asp Tyr Tyr Gly Asp
    530                 535                 540

Asp Ala Ser Tyr Thr Asn Leu Met Ala Ser Tyr Gly Thr Lys His Ser
545                 550                 555                 560

Ala Asp Ser Trp Trp Lys Thr Gly Arg Val Pro Arg Ile Ser Cys Gly
                565                 570                 575

Ile Asn Tyr Gly Phe Asp Arg Phe Lys Gly Ser Gly Pro Gly Tyr Tyr
            580                 585                 590

Arg Leu Thr Leu Ile Ala Asn Gly Tyr Arg Asp Val Val Ala Asp Val
        595                 600                 605

Arg Phe Leu Pro Lys Tyr Glu Gly Asn Ile Asp Ile Gly Leu Lys Gly
    610                 615                 620

Lys Val Leu Thr Ile Gly Gly Ala Asp Ala Glu Thr Leu Met Asp Ala
625                 630                 635                 640

Ala Val Asp Val Phe Ala Asp Gly Gln Pro Lys Leu Val Ser Asp Gln
                645                 650                 655

Ala Val Ser Leu Gly Gln Asn Val Leu Ser Ala Asp Phe Thr Pro Gly
            660                 665                 670

Thr Glu Tyr Thr Val Glu Val Arg Phe Lys Glu Phe Gly Ser Val Arg
        675                 680                 685

Ala Lys Val Val Ala Gln Leu Ala Thr Lys Ala Val Ser Val Leu Lys
    690                 695                 700
```

-continued

Gly Asp Gly Pro Val Gln Gly Ile Ile Asn Phe Glu Gln Lys Glu Ser
705 710 715 720

Asn Gly Pro Val Lys Val Trp Gly Ser Ile Lys Gly Leu Thr Glu Gly
725 730 735

Leu His Gly Phe His Val His Glu Phe Gly Asp Asn Thr Ala Gly Cys
740 745 750

Thr Ser Ala Gly Pro His Phe Asn Pro Leu Ser Arg Lys His Gly Gly
755 760 765

Pro Lys Asp Glu Glu Arg His Val Gly Asp Leu Gly Asn Val Thr Ala
770 775 780

Asp Lys Asp Gly Val Ala Asp Val Ser Ile Glu Asp Ser Val Ile Ser
785 790 795 800

Leu Ser Gly Asp His Ser Ile Ile Gly Arg Thr Leu Val Val His Glu
805 810 815

Lys Ala Asp Asp Leu Gly Lys Gly Gly Asn Glu Glu Ser Thr Lys Thr
820 825 830

Gly Asn Ala Gly Ser Arg Leu Ala Cys Gly Val Ile Gly Ile Ala Gln
835 840 845

<210> SEQ ID NO 8
<211> LENGTH: 846
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(139)
<223> OTHER INFORMATION: Treponema pallidum outer membrane protein TP15
<220> FEATURE:
<221> NAME/KEY: MISC_FEATURE
<222> LOCATION: (143)..(556)
<223> OTHER INFORMATION: Treponema pallidum outer membrane protein TP47
<220> FEATURE:
<221> NAME/KEY: MISC_FEATURE
<222> LOCATION: (559)..(692)
<223> OTHER INFORMATION: Treponema pallidum outer membrane protein TP17
<220> FEATURE:
<221> NAME/KEY: MISC_FEATURE
<222> LOCATION: (694)..(846)
<223> OTHER INFORMATION: human copper zinc superoxide dismutase

<400> SEQUENCE: 8

Met Arg Gly Ser Ala Val Pro Pro Gln Gln Trp Ala Leu Ser Gly Ser
1 5 10 15

Ser Phe Ser Ser Ile Pro Asn Gly Thr Tyr Arg Ala Thr Tyr Gln Asp
20 25 30

Phe Asp Glu Asn Gly Trp Lys Asp Phe Leu Glu Val Thr Phe Asp Gly
35 40 45

Gly Lys Met Val Gln Val Val Tyr Asp Tyr Gln His Lys Glu Gly Arg
50 55 60

Phe Lys Ser Gln Asp Ala Asp Tyr His Arg Val Met Tyr Ala Ser Ser
65 70 75 80

Gly Ile Gly Pro Glu Lys Ala Phe Arg Glu Leu Ala Asp Ala Leu Leu
85 90 95

Glu Lys Gly Asn Pro Glu Met Val Asp Val Val Thr Gly Ala Thr Val
100 105 110

Ser Ser Gln Ser Phe Arg Arg Leu Gly Arg Ala Leu Leu Gln Ser Ala
115 120 125

Arg Arg Gly Glu Lys Glu Ala Ile Ile Ser Arg Gly Arg Ser Gly Ser

-continued

```
    130                 135                 140

Ser His His Glu Thr His Tyr Gly Tyr Ala Thr Leu Ser Tyr Ala Asp
145                 150                 155                 160

Tyr Trp Ala Gly Glu Leu Gly Gln Ser Arg Asp Val Leu Leu Ala Gly
                165                 170                 175

Asn Ala Glu Ala Asp Arg Ala Gly Asp Leu Asp Ala Gly Met Phe Asp
            180                 185                 190

Ala Val Ser Arg Ala Thr His Gly His Gly Ala Phe Arg Gln Gln Phe
        195                 200                 205

Gln Tyr Ala Val Glu Val Leu Gly Glu Lys Val Leu Ser Lys Gln Glu
    210                 215                 220

Thr Glu Asp Ser Arg Gly Arg Lys Lys Trp Glu Tyr Glu Thr Asp Pro
225                 230                 235                 240

Ser Val Thr Lys Met Val Arg Ala Ser Ala Ser Phe Gln Asp Leu Gly
                245                 250                 255

Glu Asp Gly Glu Ile Lys Phe Glu Ala Val Glu Gly Ala Val Ala Leu
            260                 265                 270

Ala Asp Arg Ala Ser Ser Phe Met Val Asp Ser Glu Glu Tyr Lys Ile
        275                 280                 285

Thr Asn Val Lys Val His Gly Met Lys Phe Val Pro Val Ala Val Pro
    290                 295                 300

His Glu Leu Lys Gly Ile Ala Lys Glu Lys Phe His Phe Val Glu Asp
305                 310                 315                 320

Ser Arg Val Thr Glu Asn Thr Asn Gly Leu Lys Thr Met Leu Thr Glu
                325                 330                 335

Asp Ser Phe Ser Ala Arg Lys Val Ser Ser Met Glu Ser Pro His Asp
            340                 345                 350

Leu Val Val Asp Thr Val Gly Thr Gly Tyr His Ser Arg Phe Gly Ser
        355                 360                 365

Asp Ala Glu Ala Ser Val Met Leu Lys Arg Ala Asp Gly Ser Glu Leu
    370                 375                 380

Ser His Arg Glu Phe Ile Asp Tyr Val Met Asn Phe Asn Thr Val Arg
385                 390                 395                 400

Tyr Asp Tyr Tyr Gly Asp Asp Ala Ser Tyr Thr Asn Leu Met Ala Ser
                405                 410                 415

Tyr Gly Thr Lys His Ser Ala Asp Ser Trp Trp Lys Thr Gly Arg Val
            420                 425                 430

Pro Arg Ile Ser Cys Gly Ile Asn Tyr Gly Phe Asp Arg Phe Lys Gly
        435                 440                 445

Ser Gly Pro Gly Tyr Tyr Arg Leu Thr Leu Ile Ala Asn Gly Tyr Arg
    450                 455                 460

Asp Val Val Ala Asp Val Arg Phe Leu Pro Lys Tyr Glu Gly Asn Ile
465                 470                 475                 480

Asp Ile Gly Leu Lys Gly Lys Val Leu Thr Ile Gly Gly Ala Asp Ala
                485                 490                 495

Glu Thr Leu Met Asp Ala Ala Val Asp Val Phe Ala Asp Gly Gln Pro
            500                 505                 510

Lys Leu Val Ser Asp Gln Ala Val Ser Leu Gly Gln Asn Val Leu Ser
        515                 520                 525

Ala Asp Phe Thr Pro Gly Thr Glu Tyr Thr Val Glu Val Arg Phe Lys
    530                 535                 540

Glu Phe Gly Ser Val Arg Ala Lys Val Val Ala Gln Gly Pro Val Ser
545                 550                 555                 560
```

-continued

```
Cys Thr Thr Val Cys Pro His Ala Gly Lys Ala Lys Ala Glu Lys Val
                565                 570                 575

Glu Cys Ala Leu Lys Gly Gly Ile Phe Arg Gly Thr Leu Pro Ala Ala
            580                 585                 590

Asp Cys Pro Gly Ile Asp Thr Thr Val Thr Phe Asn Ala Asp Gly Thr
        595                 600                 605

Ala Gln Lys Val Glu Leu Ala Leu Glu Lys Lys Ser Ala Pro Ser Pro
    610                 615                 620

Leu Thr Tyr Arg Gly Thr Trp Met Val Arg Glu Asp Gly Ile Val Glu
625                 630                 635                 640

Leu Ser Leu Val Ser Ser Glu Gln Ser Lys Ala Pro His Glu Lys Glu
                645                 650                 655

Leu Tyr Glu Leu Ile Asp Ser Asn Ser Val Arg Tyr Met Gly Ala Pro
            660                 665                 670

Gly Ala Gly Lys Pro Ser Lys Glu Met Ala Pro Phe Tyr Val Leu Lys
        675                 680                 685

Lys Thr Lys Lys Leu Ala Thr Lys Ala Val Ser Val Leu Lys Gly Asp
    690                 695                 700

Gly Pro Val Gln Gly Ile Ile Asn Phe Glu Gln Lys Glu Ser Asn Gly
705                 710                 715                 720

Pro Val Lys Val Trp Gly Ser Ile Lys Gly Leu Thr Glu Gly Leu His
                725                 730                 735

Gly Phe His Val His Glu Phe Gly Asp Asn Thr Ala Gly Cys Thr Ser
            740                 745                 750

Ala Gly Pro His Phe Asn Pro Leu Ser Arg Lys His Gly Gly Pro Lys
        755                 760                 765

Asp Glu Glu Arg His Val Gly Asp Leu Gly Asn Val Thr Ala Asp Lys
    770                 775                 780

Asp Gly Val Ala Asp Val Ser Ile Glu Asp Ser Val Ile Ser Leu Ser
785                 790                 795                 800

Gly Asp His Ser Ile Ile Gly Arg Thr Leu Val Val His Glu Lys Ala
                805                 810                 815

Asp Asp Leu Gly Lys Gly Gly Asn Glu Glu Ser Thr Lys Thr Gly Asn
            820                 825                 830

Ala Gly Ser Arg Leu Ala Cys Gly Val Ile Gly Ile Ala Gln
        835                 840                 845
```

<210> SEQ ID NO 9
<211> LENGTH: 849
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(150)
<223> OTHER INFORMATION: Treponema pallidum outer membrane protein TP17
<220> FEATURE:
<221> NAME/KEY: MISC_FEATURE
<222> LOCATION: (155)..(277)
<223> OTHER INFORMATION: Treponema pallidum outer membrane protein TP15
<220> FEATURE:
<221> NAME/KEY: MISC_FEATURE
<222> LOCATION: (282)..(695)
<223> OTHER INFORMATION: Treponema pallidum outer membrane protein TP47
<220> FEATURE:
<221> NAME/KEY: MISC_FEATURE
<222> LOCATION: (697)..(849)
<223> OTHER INFORMATION: human copper zinc superoxide dismutase -continued

<400> SEQUENCE: 9

```
Met Arg Gly Ser Ala Val Pro Pro Gln Gln Trp Ala Leu Ser Gly Ser
1               5                   10                  15

Val Ser Cys Thr Thr Val Cys Pro His Ala Gly Lys Ala Lys Ala Glu
            20                  25                  30

Lys Val Glu Cys Ala Leu Lys Gly Gly Ile Phe Arg Gly Thr Leu Pro
        35                  40                  45

Ala Ala Asp Cys Pro Gly Ile Asp Thr Thr Val Thr Phe Asn Ala Asp
    50                  55                  60

Gly Thr Ala Gln Lys Val Glu Leu Ala Leu Glu Lys Lys Ser Ala Pro
65                  70                  75                  80

Ser Pro Leu Thr Tyr Arg Gly Thr Trp Met Val Arg Glu Asp Gly Ile
                85                  90                  95

Val Glu Leu Ser Leu Val Ser Ser Glu Gln Ser Lys Ala Pro His Glu
            100                 105                 110

Lys Glu Leu Tyr Glu Leu Ile Asp Ser Asn Ser Val Arg Tyr Met Gly
        115                 120                 125

Ala Pro Gly Ala Gly Lys Pro Ser Lys Glu Met Ala Pro Phe Tyr Val
    130                 135                 140

Leu Lys Lys Thr Lys Lys Gly Pro Arg Ser Ser Phe Ser Ser Ile Pro
145                 150                 155                 160

Asn Gly Thr Tyr Arg Ala Thr Tyr Gln Asp Phe Asp Glu Asn Gly Trp
                165                 170                 175

Lys Asp Phe Leu Glu Val Thr Phe Asp Gly Gly Lys Met Val Gln Val
            180                 185                 190

Val Tyr Asp Tyr Gln His Lys Glu Gly Arg Phe Lys Ser Gln Asp Ala
        195                 200                 205

Asp Tyr His Arg Val Met Tyr Ala Ser Ser Gly Ile Gly Pro Glu Lys
    210                 215                 220

Ala Phe Arg Glu Leu Ala Asp Ala Leu Leu Glu Lys Gly Asn Pro Glu
225                 230                 235                 240

Met Val Asp Val Val Thr Gly Ala Thr Val Ser Ser Gln Ser Phe Arg
                245                 250                 255

Arg Leu Gly Arg Ala Leu Leu Gln Ser Ala Arg Arg Gly Glu Lys Glu
            260                 265                 270

Ala Ile Ile Ser Arg Gly Pro Arg Ser Gly Ser Ser His His Glu Thr
        275                 280                 285

His Tyr Gly Tyr Ala Thr Leu Ser Tyr Ala Asp Tyr Trp Ala Gly Glu
    290                 295                 300

Leu Gly Gln Ser Arg Asp Val Leu Leu Ala Gly Asn Ala Glu Ala Asp
305                 310                 315                 320

Arg Ala Gly Asp Leu Asp Ala Gly Met Phe Asp Ala Val Ser Arg Ala
                325                 330                 335

Thr His Gly His Gly Ala Phe Arg Gln Gln Phe Gln Tyr Ala Val Glu
            340                 345                 350

Val Leu Gly Glu Lys Val Leu Ser Lys Gln Glu Thr Glu Asp Ser Arg
        355                 360                 365

Gly Arg Lys Lys Trp Glu Tyr Glu Thr Asp Pro Ser Val Thr Lys Met
    370                 375                 380

Val Arg Ala Ser Ala Ser Phe Gln Asp Leu Gly Glu Asp Gly Glu Ile
385                 390                 395                 400

Lys Phe Glu Ala Val Glu Gly Ala Val Ala Leu Ala Asp Arg Ala Ser
                405                 410                 415
```

-continued

```
Ser Phe Met Val Asp Ser Glu Glu Tyr Lys Ile Thr Asn Val Lys Val
            420                 425                 430

His Gly Met Lys Phe Val Pro Val Ala Val Pro His Glu Leu Lys Gly
        435                 440                 445

Ile Ala Lys Glu Lys Phe His Phe Val Glu Asp Ser Arg Val Thr Glu
    450                 455                 460

Asn Thr Asn Gly Leu Lys Thr Met Leu Thr Glu Asp Ser Phe Ser Ala
465                 470                 475                 480

Arg Lys Val Ser Ser Met Glu Ser Pro His Asp Leu Val Val Asp Thr
                485                 490                 495

Val Gly Thr Gly Tyr His Ser Arg Phe Gly Ser Asp Ala Glu Ala Ser
            500                 505                 510

Val Met Leu Lys Arg Ala Asp Gly Ser Glu Leu Ser His Arg Glu Phe
        515                 520                 525

Ile Asp Tyr Val Met Asn Phe Asn Thr Val Arg Tyr Asp Tyr Tyr Gly
    530                 535                 540

Asp Asp Ala Ser Tyr Thr Asn Leu Met Ala Ser Tyr Gly Thr Lys His
545                 550                 555                 560

Ser Ala Asp Ser Trp Trp Lys Thr Gly Arg Val Pro Arg Ile Ser Cys
                565                 570                 575

Gly Ile Asn Tyr Gly Phe Asp Arg Phe Lys Gly Ser Gly Pro Gly Tyr
            580                 585                 590

Tyr Arg Leu Thr Leu Ile Ala Asn Gly Tyr Arg Asp Val Val Ala Asp
        595                 600                 605

Val Arg Phe Leu Pro Lys Tyr Glu Gly Asn Ile Asp Ile Gly Leu Lys
    610                 615                 620

Gly Lys Val Leu Thr Ile Gly Gly Ala Asp Ala Glu Thr Leu Met Asp
625                 630                 635                 640

Ala Ala Val Asp Val Phe Ala Asp Gly Gln Pro Lys Leu Val Ser Asp
                645                 650                 655

Gln Ala Val Ser Leu Gly Gln Asn Val Leu Ser Ala Asp Phe Thr Pro
            660                 665                 670

Gly Thr Glu Tyr Thr Val Glu Val Arg Phe Lys Glu Phe Gly Ser Val
        675                 680                 685

Arg Ala Lys Val Val Ala Gln Leu Ala Thr Lys Ala Val Ser Val Leu
    690                 695                 700

Lys Gly Asp Gly Pro Val Gln Gly Ile Ile Asn Phe Glu Gln Lys Glu
705                 710                 715                 720

Ser Asn Gly Pro Val Lys Val Trp Gly Ser Ile Lys Gly Leu Thr Glu
                725                 730                 735

Gly Leu His Gly Phe His Val His Glu Phe Gly Asp Asn Thr Ala Gly
            740                 745                 750

Cys Thr Ser Ala Gly Pro His Phe Asn Pro Leu Ser Arg Lys His Gly
        755                 760                 765

Gly Pro Lys Asp Glu Glu Arg His Val Gly Asp Leu Gly Asn Val Thr
    770                 775                 780

Ala Asp Lys Asp Gly Val Ala Asp Val Ser Ile Glu Asp Ser Val Ile
785                 790                 795                 800

Ser Leu Ser Gly Asp His Ser Ile Ile Gly Arg Thr Leu Val Val His
                805                 810                 815

Glu Lys Ala Asp Asp Leu Gly Lys Gly Gly Asn Glu Glu Ser Thr Lys
            820                 825                 830

Thr Gly Asn Ala Gly Ser Arg Leu Ala Cys Gly Val Ile Gly Ile Ala
        835                 840                 845
```

-continued

Gln

<210> SEQ ID NO 10
<211> LENGTH: 847
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(150)
<223> OTHER INFORMATION: Treponema pallidum outer membrane protein TP17
<220> FEATURE:
<221> NAME/KEY: MISC_FEATURE
<222> LOCATION: (155)..(568)
<223> OTHER INFORMATION: Treponema pallidum outer membrane protein TP47
<220> FEATURE:
<221> NAME/KEY: MISC_FEATURE
<222> LOCATION: (571)..(693)
<223> OTHER INFORMATION: Treponema pallidum outer membrane protein TP15
<220> FEATURE:
<221> NAME/KEY: MISC_FEATURE
<222> LOCATION: (695)..(847)
<223> OTHER INFORMATION: human copper zinc superoxide dismutase

<400> SEQUENCE: 10

Met Arg Gly Ser Ala Val Pro Pro Gln Gln Trp Ala Leu Ser Gly Ser
1 5 10 15

Val Ser Cys Thr Thr Val Cys Pro His Ala Gly Lys Ala Lys Ala Glu
20 25 30

Lys Val Glu Cys Ala Leu Lys Gly Gly Ile Phe Arg Gly Thr Leu Pro
35 40 45

Ala Ala Asp Cys Pro Gly Ile Asp Thr Thr Val Thr Phe Asn Ala Asp
50 55 60

Gly Thr Ala Gln Lys Val Glu Leu Ala Leu Glu Lys Lys Ser Ala Pro
65 70 75 80

Ser Pro Leu Thr Tyr Arg Gly Thr Trp Met Val Arg Glu Asp Gly Ile
85 90 95

Val Glu Leu Ser Leu Val Ser Ser Glu Gln Ser Lys Ala Pro His Glu
100 105 110

Lys Glu Leu Tyr Glu Leu Ile Asp Ser Asn Ser Val Arg Tyr Met Gly
115 120 125

Ala Pro Gly Ala Gly Lys Pro Ser Lys Glu Met Ala Pro Phe Tyr Val
130 135 140

Leu Lys Lys Thr Lys Lys Gly Pro Arg Ser Gly Ser Ser His His Glu
145 150 155 160

Thr His Tyr Gly Tyr Ala Thr Leu Ser Tyr Ala Asp Tyr Trp Ala Gly
165 170 175

Glu Leu Gly Gln Ser Arg Asp Val Leu Leu Ala Gly Asn Ala Glu Ala
180 185 190

Asp Arg Ala Gly Asp Leu Asp Ala Gly Met Phe Asp Ala Val Ser Arg
195 200 205

Ala Thr His Gly His Gly Ala Phe Arg Gln Gln Phe Gln Tyr Ala Val
210 215 220

Glu Val Leu Gly Glu Lys Val Leu Ser Lys Gln Glu Thr Glu Asp Ser
225 230 235 240

Arg Gly Arg Lys Lys Trp Glu Tyr Glu Thr Asp Pro Ser Val Thr Lys
245 250 255

Met Val Arg Ala Ser Ala Ser Phe Gln Asp Leu Gly Glu Asp Gly Glu

-continued

```
            260                 265                 270

Ile Lys Phe Glu Ala Val Glu Gly Ala Val Ala Leu Ala Asp Arg Ala
        275                 280                 285

Ser Ser Phe Met Val Asp Ser Glu Glu Tyr Lys Ile Thr Asn Val Lys
    290                 295                 300

Val His Gly Met Lys Phe Val Pro Val Ala Val Pro His Glu Leu Lys
305                 310                 315                 320

Gly Ile Ala Lys Glu Lys Phe His Phe Val Glu Asp Ser Arg Val Thr
                325                 330                 335

Glu Asn Thr Asn Gly Leu Lys Thr Met Leu Thr Glu Asp Ser Phe Ser
            340                 345                 350

Ala Arg Lys Val Ser Ser Met Glu Ser Pro His Asp Leu Val Val Asp
        355                 360                 365

Thr Val Gly Thr Gly Tyr His Ser Arg Phe Gly Ser Asp Ala Glu Ala
    370                 375                 380

Ser Val Met Leu Lys Arg Ala Asp Gly Ser Glu Leu Ser His Arg Glu
385                 390                 395                 400

Phe Ile Asp Tyr Val Met Asn Phe Asn Thr Val Arg Tyr Asp Tyr Tyr
                405                 410                 415

Gly Asp Asp Ala Ser Tyr Thr Asn Leu Met Ala Ser Tyr Gly Thr Lys
            420                 425                 430

His Ser Ala Asp Ser Trp Trp Lys Thr Gly Arg Val Pro Arg Ile Ser
        435                 440                 445

Cys Gly Ile Asn Tyr Gly Phe Asp Arg Phe Lys Gly Ser Gly Pro Gly
    450                 455                 460

Tyr Tyr Arg Leu Thr Leu Ile Ala Asn Gly Tyr Arg Asp Val Val Ala
465                 470                 475                 480

Asp Val Arg Phe Leu Pro Lys Tyr Glu Gly Asn Ile Asp Ile Gly Leu
                485                 490                 495

Lys Gly Lys Val Leu Thr Ile Gly Gly Ala Asp Ala Glu Thr Leu Met
            500                 505                 510

Asp Ala Ala Val Asp Val Phe Ala Asp Gly Gln Pro Lys Leu Val Ser
        515                 520                 525

Asp Gln Ala Val Ser Leu Gly Gln Asn Val Leu Ser Ala Asp Phe Thr
    530                 535                 540

Pro Gly Thr Glu Tyr Thr Val Glu Val Arg Phe Lys Glu Phe Gly Ser
545                 550                 555                 560

Val Arg Ala Lys Val Val Ala Gln Gly Pro Ser Phe Ser Ser Ile Pro
                565                 570                 575

Asn Gly Thr Tyr Arg Ala Thr Tyr Gln Asp Phe Asp Glu Asn Gly Trp
            580                 585                 590

Lys Asp Phe Leu Glu Val Thr Phe Asp Gly Gly Lys Met Val Gln Val
        595                 600                 605

Val Tyr Asp Tyr Gln His Lys Glu Gly Arg Phe Lys Ser Gln Asp Ala
    610                 615                 620

Asp Tyr His Arg Val Met Tyr Ala Ser Ser Gly Ile Gly Pro Glu Lys
625                 630                 635                 640

Ala Phe Arg Glu Leu Ala Asp Ala Leu Leu Glu Lys Gly Asn Pro Glu
                645                 650                 655

Met Val Asp Val Val Thr Gly Ala Thr Val Ser Ser Gln Ser Phe Arg
            660                 665                 670

Arg Leu Gly Arg Ala Leu Leu Gln Ser Ala Arg Arg Gly Glu Lys Glu
        675                 680                 685
```

Ala Ile Ile Ser Arg Leu Ala Thr Lys Ala Val Ser Val Leu Lys Gly
    690                 695                 700

Asp Gly Pro Val Gln Gly Ile Ile Asn Phe Glu Gln Lys Glu Ser Asn
705                 710                 715                 720

Gly Pro Val Lys Val Trp Gly Ser Ile Lys Gly Leu Thr Glu Gly Leu
                725                 730                 735

His Gly Phe His Val His Glu Phe Gly Asp Asn Thr Ala Gly Cys Thr
            740                 745                 750

Ser Ala Gly Pro His Phe Asn Pro Leu Ser Arg Lys His Gly Gly Pro
        755                 760                 765

Lys Asp Glu Glu Arg His Val Gly Asp Leu Gly Asn Val Thr Ala Asp
    770                 775                 780

Lys Asp Gly Val Ala Asp Val Ser Ile Glu Asp Ser Val Ile Ser Leu
785                 790                 795                 800

Ser Gly Asp His Ser Ile Ile Gly Arg Thr Leu Val Val His Glu Lys
                805                 810                 815

Ala Asp Asp Leu Gly Lys Gly Gly Asn Glu Glu Ser Thr Lys Thr Gly
            820                 825                 830

Asn Ala Gly Ser Arg Leu Ala Cys Gly Val Ile Gly Ile Ala Gln
        835                 840                 845

<210> SEQ ID NO 11
<211> LENGTH: 847
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(430)
<223> OTHER INFORMATION: Treponema pallidum outer membrane protein TP47
<220> FEATURE:
<221> NAME/KEY: MISC_FEATURE
<222> LOCATION: (435)..(557)
<223> OTHER INFORMATION: Treponema pallidum outer membrane protein TP15
<220> FEATURE:
<221> NAME/KEY: MISC_FEATURE
<222> LOCATION: (560)..(693)
<223> OTHER INFORMATION: Treponema pallidum outer membrane protein TP17
<220> FEATURE:
<221> NAME/KEY: MISC_FEATURE
<222> LOCATION: (695)..(847)
<223> OTHER INFORMATION: human copper zinc superoxide dismutase

<400> SEQUENCE: 11

Met Arg Gly Ser Ala Val Pro Pro Gln Gln Trp Ala Leu Ser Gly Ser
1               5                   10                  15

Gly Ser Ser His His Glu Thr His Tyr Gly Tyr Ala Thr Leu Ser Tyr
            20                  25                  30

Ala Asp Tyr Trp Ala Gly Glu Leu Gly Gln Ser Arg Asp Val Leu Leu
        35                  40                  45

Ala Gly Asn Ala Glu Ala Asp Arg Ala Gly Asp Leu Asp Ala Gly Met
    50                  55                  60

Phe Asp Ala Val Ser Arg Ala Thr His Gly His Gly Ala Phe Arg Gln
65                  70                  75                  80

Gln Phe Gln Tyr Ala Val Glu Val Leu Gly Glu Lys Val Leu Ser Lys
                85                  90                  95

Gln Glu Thr Glu Asp Ser Arg Gly Arg Lys Lys Trp Glu Tyr Glu Thr
            100                 105                 110

Asp Pro Ser Val Thr Lys Met Val Arg Ala Ser Ala Ser Phe Gln Asp

-continued

```
        115                 120                 125

Leu Gly Glu Asp Gly Glu Ile Lys Phe Glu Ala Val Glu Gly Ala Val
    130                 135                 140

Ala Leu Ala Asp Arg Ala Ser Ser Phe Met Val Asp Ser Glu Glu Tyr
145                 150                 155                 160

Lys Ile Thr Asn Val Lys Val His Gly Met Lys Phe Val Pro Val Ala
                165                 170                 175

Val Pro His Glu Leu Lys Gly Ile Ala Lys Glu Lys Phe His Phe Val
            180                 185                 190

Glu Asp Ser Arg Val Thr Glu Asn Thr Asn Gly Leu Lys Thr Met Leu
        195                 200                 205

Thr Glu Asp Ser Phe Ser Ala Arg Lys Val Ser Ser Met Glu Ser Pro
    210                 215                 220

His Asp Leu Val Val Asp Thr Val Gly Thr Gly Tyr His Ser Arg Phe
225                 230                 235                 240

Gly Ser Asp Ala Glu Ala Ser Val Met Leu Lys Arg Ala Asp Gly Ser
                245                 250                 255

Glu Leu Ser His Arg Glu Phe Ile Asp Tyr Val Met Asn Phe Asn Thr
            260                 265                 270

Val Arg Tyr Asp Tyr Tyr Gly Asp Asp Ala Ser Tyr Thr Asn Leu Met
        275                 280                 285

Ala Ser Tyr Gly Thr Lys His Ser Ala Asp Ser Trp Trp Lys Thr Gly
    290                 295                 300

Arg Val Pro Arg Ile Ser Cys Gly Ile Asn Tyr Gly Phe Asp Arg Phe
305                 310                 315                 320

Lys Gly Ser Gly Pro Gly Tyr Tyr Arg Leu Thr Leu Ile Ala Asn Gly
                325                 330                 335

Tyr Arg Asp Val Val Ala Asp Val Arg Phe Leu Pro Lys Tyr Glu Gly
            340                 345                 350

Asn Ile Asp Ile Gly Leu Lys Gly Lys Val Leu Thr Ile Gly Gly Ala
        355                 360                 365

Asp Ala Glu Thr Leu Met Asp Ala Ala Val Asp Val Phe Ala Asp Gly
    370                 375                 380

Gln Pro Lys Leu Val Ser Asp Gln Ala Val Ser Leu Gly Gln Asn Val
385                 390                 395                 400

Leu Ser Ala Asp Phe Thr Pro Gly Thr Glu Tyr Thr Val Glu Val Arg
                405                 410                 415

Phe Lys Glu Phe Gly Ser Val Arg Ala Lys Val Val Ala Gln Gly Pro
            420                 425                 430

Arg Ser Ser Phe Ser Ser Ile Pro Asn Gly Thr Tyr Arg Ala Thr Tyr
        435                 440                 445

Gln Asp Phe Asp Glu Asn Gly Trp Lys Asp Phe Leu Glu Val Thr Phe
    450                 455                 460

Asp Gly Gly Lys Met Val Gln Val Val Tyr Asp Tyr Gln His Lys Glu
465                 470                 475                 480

Gly Arg Phe Lys Ser Gln Asp Ala Asp Tyr His Arg Val Met Tyr Ala
                485                 490                 495

Ser Ser Gly Ile Gly Pro Glu Lys Ala Phe Arg Glu Leu Ala Asp Ala
            500                 505                 510

Leu Leu Glu Lys Gly Asn Pro Glu Met Val Asp Val Val Thr Gly Ala
        515                 520                 525

Thr Val Ser Ser Gln Ser Phe Arg Arg Leu Gly Arg Ala Leu Leu Gln
    530                 535                 540
```

-continued

```
Ser Ala Arg Arg Gly Glu Lys Glu Ala Ile Ile Ser Arg Gly Pro Val
545                 550                 555                 560

Ser Cys Thr Thr Val Cys Pro His Ala Gly Lys Ala Lys Ala Glu Lys
                565                 570                 575

Val Glu Cys Ala Leu Lys Gly Gly Ile Phe Arg Gly Thr Leu Pro Ala
            580                 585                 590

Ala Asp Cys Pro Gly Ile Asp Thr Thr Val Thr Phe Asn Ala Asp Gly
        595                 600                 605

Thr Ala Gln Lys Val Glu Leu Ala Leu Glu Lys Lys Ser Ala Pro Ser
    610                 615                 620

Pro Leu Thr Tyr Arg Gly Thr Trp Met Val Arg Glu Asp Gly Ile Val
625                 630                 635                 640

Glu Leu Ser Leu Val Ser Ser Glu Gln Ser Lys Ala Pro His Glu Lys
                645                 650                 655

Glu Leu Tyr Glu Leu Ile Asp Ser Asn Ser Val Arg Tyr Met Gly Ala
            660                 665                 670

Pro Gly Ala Gly Lys Pro Ser Lys Glu Met Ala Pro Phe Tyr Val Leu
        675                 680                 685

Lys Lys Thr Lys Lys Leu Ala Thr Lys Ala Val Ser Val Leu Lys Gly
    690                 695                 700

Asp Gly Pro Val Gln Gly Ile Ile Asn Phe Glu Gln Lys Glu Ser Asn
705                 710                 715                 720

Gly Pro Val Lys Val Trp Gly Ser Ile Lys Gly Leu Thr Glu Gly Leu
                725                 730                 735

His Gly Phe His Val His Glu Phe Gly Asp Asn Thr Ala Gly Cys Thr
            740                 745                 750

Ser Ala Gly Pro His Phe Asn Pro Leu Ser Arg Lys His Gly Gly Pro
        755                 760                 765

Lys Asp Glu Glu Arg His Val Gly Asp Leu Gly Asn Val Thr Ala Asp
    770                 775                 780

Lys Asp Gly Val Ala Asp Val Ser Ile Glu Asp Ser Val Ile Ser Leu
785                 790                 795                 800

Ser Gly Asp His Ser Ile Ile Gly Arg Thr Leu Val Val His Glu Lys
                805                 810                 815

Ala Asp Asp Leu Gly Lys Gly Gly Asn Glu Glu Ser Thr Lys Thr Gly
            820                 825                 830

Asn Ala Gly Ser Arg Leu Ala Cys Gly Val Ile Gly Ile Ala Gln
        835                 840                 845
```

<210> SEQ ID NO 12
<211> LENGTH: 849
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(430)
<223> OTHER INFORMATION: Treponema pallidum outer membrane protein TP47
<220> FEATURE:
<221> NAME/KEY: MISC_FEATURE
<222> LOCATION: (435)..(568)
<223> OTHER INFORMATION: Treponema pallidum outer membrane protein TP17
<220> FEATURE:
<221> NAME/KEY: MISC_FEATURE
<222> LOCATION: (573)..(695)
<223> OTHER INFORMATION: Treponema pallidum outer membrane protein TP15
<220> FEATURE:
<221> NAME/KEY: MISC_FEATURE
<222> LOCATION: (697)..(849)
<223> OTHER INFORMATION: human copper zinc superoxide dismutase

<400> SEQUENCE: 12

```
Met Arg Gly Ser Ala Val Pro Pro Gln Gln Trp Ala Leu Ser Gly Ser
1               5                   10                  15

Gly Ser Ser His His Glu Thr His Tyr Gly Tyr Ala Thr Leu Ser Tyr
            20                  25                  30

Ala Asp Tyr Trp Ala Gly Glu Leu Gly Gln Ser Arg Asp Val Leu Leu
        35                  40                  45

Ala Gly Asn Ala Glu Ala Asp Arg Ala Gly Asp Leu Asp Ala Gly Met
    50                  55                  60

Phe Asp Ala Val Ser Arg Ala Thr His Gly His Gly Ala Phe Arg Gln
65                  70                  75                  80

Gln Phe Gln Tyr Ala Val Glu Val Leu Gly Glu Lys Val Leu Ser Lys
                85                  90                  95

Gln Glu Thr Glu Asp Ser Arg Gly Arg Lys Lys Trp Glu Tyr Glu Thr
            100                 105                 110

Asp Pro Ser Val Thr Lys Met Val Arg Ala Ser Ala Ser Phe Gln Asp
        115                 120                 125

Leu Gly Glu Asp Gly Glu Ile Lys Phe Glu Ala Val Glu Gly Ala Val
    130                 135                 140

Ala Leu Ala Asp Arg Ala Ser Ser Phe Met Val Asp Ser Glu Glu Tyr
145                 150                 155                 160

Lys Ile Thr Asn Val Lys Val His Gly Met Lys Phe Val Pro Val Ala
                165                 170                 175

Val Pro His Glu Leu Lys Gly Ile Ala Lys Glu Lys Phe His Phe Val
            180                 185                 190

Glu Asp Ser Arg Val Thr Glu Asn Thr Asn Gly Leu Lys Thr Met Leu
        195                 200                 205

Thr Glu Asp Ser Phe Ser Ala Arg Lys Val Ser Ser Met Glu Ser Pro
    210                 215                 220

His Asp Leu Val Val Asp Thr Val Gly Thr Gly Tyr His Ser Arg Phe
225                 230                 235                 240

Gly Ser Asp Ala Glu Ala Ser Val Met Leu Lys Arg Ala Asp Gly Ser
                245                 250                 255

Glu Leu Ser His Arg Glu Phe Ile Asp Tyr Val Met Asn Phe Asn Thr
            260                 265                 270

Val Arg Tyr Asp Tyr Tyr Gly Asp Asp Ala Ser Tyr Thr Asn Leu Met
        275                 280                 285

Ala Ser Tyr Gly Thr Lys His Ser Ala Asp Ser Trp Trp Lys Thr Gly
    290                 295                 300

Arg Val Pro Arg Ile Ser Cys Gly Ile Asn Tyr Gly Phe Asp Arg Phe
305                 310                 315                 320

Lys Gly Ser Gly Pro Gly Tyr Tyr Arg Leu Thr Leu Ile Ala Asn Gly
                325                 330                 335

Tyr Arg Asp Val Val Ala Asp Val Arg Phe Leu Pro Lys Tyr Glu Gly
            340                 345                 350

Asn Ile Asp Ile Gly Leu Lys Gly Lys Val Leu Thr Ile Gly Gly Ala
        355                 360                 365

Asp Ala Glu Thr Leu Met Asp Ala Ala Val Asp Val Phe Ala Asp Gly
    370                 375                 380

Gln Pro Lys Leu Val Ser Asp Gln Ala Val Ser Leu Gly Gln Asn Val
385                 390                 395                 400
```

-continued

```
Leu Ser Ala Asp Phe Thr Pro Gly Thr Glu Tyr Thr Val Glu Val Arg
                405                 410                 415

Phe Lys Glu Phe Gly Ser Val Arg Ala Lys Val Val Ala Gln Gly Pro
            420                 425                 430

Arg Ser Val Ser Cys Thr Thr Val Cys Pro His Ala Gly Lys Ala Lys
        435                 440                 445

Ala Glu Lys Val Glu Cys Ala Leu Lys Gly Gly Ile Phe Arg Gly Thr
    450                 455                 460

Leu Pro Ala Ala Asp Cys Pro Gly Ile Asp Thr Thr Val Thr Phe Asn
465                 470                 475                 480

Ala Asp Gly Thr Ala Gln Lys Val Glu Leu Ala Leu Glu Lys Lys Ser
                485                 490                 495

Ala Pro Ser Pro Leu Thr Tyr Arg Gly Thr Trp Met Val Arg Glu Asp
            500                 505                 510

Gly Ile Val Glu Leu Ser Leu Val Ser Ser Glu Gln Ser Lys Ala Pro
        515                 520                 525

His Glu Lys Glu Leu Tyr Glu Leu Ile Asp Ser Asn Ser Val Arg Tyr
    530                 535                 540

Met Gly Ala Pro Gly Ala Gly Lys Pro Ser Lys Glu Met Ala Pro Phe
545                 550                 555                 560

Tyr Val Leu Lys Lys Thr Lys Lys Gly Pro Arg Ser Ser Phe Ser Ser
                565                 570                 575

Ile Pro Asn Gly Thr Tyr Arg Ala Thr Tyr Gln Asp Phe Asp Glu Asn
            580                 585                 590

Gly Trp Lys Asp Phe Leu Glu Val Thr Phe Asp Gly Gly Lys Met Val
        595                 600                 605

Gln Val Val Tyr Asp Tyr Gln His Lys Glu Gly Arg Phe Lys Ser Gln
    610                 615                 620

Asp Ala Asp Tyr His Arg Val Met Tyr Ala Ser Ser Gly Ile Gly Pro
625                 630                 635                 640

Glu Lys Ala Phe Arg Glu Leu Ala Asp Ala Leu Leu Glu Lys Gly Asn
                645                 650                 655

Pro Glu Met Val Asp Val Val Thr Gly Ala Thr Val Ser Ser Gln Ser
            660                 665                 670

Phe Arg Arg Leu Gly Arg Ala Leu Leu Gln Ser Ala Arg Arg Gly Glu
        675                 680                 685

Lys Glu Ala Ile Ile Ser Arg Leu Ala Thr Lys Ala Val Ser Val Leu
    690                 695                 700

Lys Gly Asp Gly Pro Val Gln Gly Ile Ile Asn Phe Glu Gln Lys Glu
705                 710                 715                 720

Ser Asn Gly Pro Val Lys Val Trp Gly Ser Ile Lys Gly Leu Thr Glu
                725                 730                 735

Gly Leu His Gly Phe His Val His Glu Phe Gly Asp Asn Thr Ala Gly
            740                 745                 750

Cys Thr Ser Ala Gly Pro His Phe Asn Pro Leu Ser Arg Lys His Gly
        755                 760                 765

Gly Pro Lys Asp Glu Glu Arg His Val Gly Asp Leu Gly Asn Val Thr
    770                 775                 780

Ala Asp Lys Asp Gly Val Ala Asp Val Ser Ile Glu Asp Ser Val Ile
785                 790                 795                 800

Ser Leu Ser Gly Asp His Ser Ile Ile Gly Arg Thr Leu Val Val His
                805                 810                 815

Glu Lys Ala Asp Asp Leu Gly Lys Gly Gly Asn Glu Glu Ser Thr Lys
            820                 825                 830
```

Thr Gly Asn Ala Gly Ser Arg Leu Ala Cys Gly Val Ile Gly Ile Ala
835 840 845

Gln

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cacagaattc attaaagagg agaaattaac 30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
tgtctgggcc cagcttttct agtattccga 30

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
tgtctgggcc cgtgagctgc accacggt 28

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
agctggagat ctcgggccgc gagagataat ggcttctt 38

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
gctggagatc taccgcgaga gataatggct tctt 34

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
agctggagat ctcgggcctt tcttggtttt cttcagaacg ta 42

<210> SEQ ID NO 19

-continued

<211> LENGTH: 37
<212> TYPE: DNA
<213> ORGANISM: Artificial Sequence
<220> FEATURE:
<223> OTHER INFORMATION: Primer

<400> SEQUENCE: 19
agctggagat cttggaccct gcgccaccac tttcgcg 37

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
cgcgaccgtg agctctcaga gtttt 25

<210> SEQ ID NO 21
<211> LENGTH: 54
<212> TYPE: DNA
<213> ORGANISM: Artificial Sequence
<220> FEATURE:
<223> OTHER INFORMATION: Primer

<400> SEQUENCE: 21
cagcacgctg acggctttgg tcgcgaggcg agagataatg gcttcttttt cgcc 54

<210> SEQ ID NO 22
<211> LENGTH: 17
<212> TYPE: DNA
<213> ORGANISM: Artificial Sequence
<220> FEATURE:
<223> OTHER INFORMATION: Primer

<400> SEQUENCE: 22
gtgagctgca ccacggt 17

<210> SEQ ID NO 23
<211> LENGTH: 53
<212> TYPE: DNA
<213> ORGANISM: Artificial Sequence
<220> FEATURE:
<223> OTHER INFORMATION: Primer

<400> SEQUENCE: 23
cagcacgctg acggctttgg tcgcgagttt cttggttttc ttcagaacgt aaa 53

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ggttagcgat caggccgt 18

<210> SEQ ID NO 25
<211> LENGTH: 49
<212> TYPE: DNA
<213> ORGANISM: Artificial Sequence
<220> FEATURE:
<223> OTHER INFORMATION: Primer

<400> SEQUENCE: 25

-continued cagcacgctg acggctttgg tcgcgagctg cgccaccact ttcgcgcgc 49

<210> SEQ ID NO 26
<211> LENGTH: 54
<212> TYPE: DNA
<213> ORGANISM: Artificial Sequence
<220> FEATURE:
<223> OTHER INFORMATION: Primer

<400> SEQUENCE: 26
ggcgaaaaag aagccattat ctctcgcctc gcgaccaaag ccgtcagcgt gctg 54

<210> SEQ ID NO 27
<211> LENGTH: 53
<212> TYPE: DNA
<213> ORGANISM: Artificial Sequence
<220> FEATURE:
<223> OTHER INFORMATION: Primer

<400> SEQUENCE: 27
tttacgttct gaagaaaacc aagaaactcg cgaccaaagc cgtcagcgtg ctg 53

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
gcgcgcgaaa gtggtggcgc agctcgcgac caaagccgtc agcgtgctg 49

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
tgcagtcgac gggcccggga t 21

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cgcgaccgtg agctctcaga gtttt 25

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ccctgccggc cgcagattgt 20

<210> SEQ ID NO 32
<211> LENGTH: 26
<212> TYPE: DNA
<213> ORGANISM: Artificial Sequence
<220> FEATURE:

-continued

```
<223> OTHER INFORMATION: Primer

<400> SEQUENCE: 32

ggatttcacc ccgggtaccg aatata                                    26


<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33

agccaagctt cattactggg cgataccaat aacgcca                        37
```

*TREPONEMA PALLIDUM* TRIPLET ANTIGEN

CROSS-REFERENCE TO RELATED APPLICATIONS

This application claims the benefit of U.S. Provisional Application No. 61/432,570, filed Jan. 13, 2011.

STATEMENT REGARDING FEDERALLY SPONSORED RESEARCH OR DEVELOPMENT

Not applicable.

FIELD OF THE INVENTION

The invention relates to the field of recombinant antigens, and more particularly to a *Treponema pallidum* triplet antigen construct and its use in immunoassays for the detection of syphilis.

BACKGROUND OF THE INVENTION

Over the past half century, effective antibiotic treatment programs have made syphilis relatively uncommon in the United States, with less than 7,100 primary and secondary cases diagnosed in 2003. However, recent data indicates that reported cases are again increasing in subsets of the population, and periodic epidemics of syphilis have occurred for decades. In 1995, the number of new cases of syphilis worldwide was estimated to be 12 million per year. If untreated, syphilis can evolve from localized primary lesions (chancres) to disseminated, chronic infections, including secondary, latent, and tertiary forms.

As a syphilitic infection can produce a variable range of symptoms in humans, laboratory tests are often required to definitively diagnose an infection. Due to the inability to culture the causative organism, *Treponema pallidum* (*T. pallidum*) (TP), in vitro, a need exists for the development and optimization of in vitro methods for the detection of *T. pallidum* in diverse clinical specimens [Morse, Salud Publica Mex 5(Suppl 45):S698-S708, 2003]. While enzyme-linked immunosorbent assays (ELISAs) for *Treponema* are commercially available, they exhibit varying efficiencies at different disease stages [Schmidt et al., J Clin Microbiol 38:1279-1282 (2000)]. Several ELISAs based on whole cell lysate were developed which presented sensitivity of 93.3% to 100% and specificity of 95.5% to 99.8% [Castro et al., J Clin Microbiol 41:250-253 (2003)].

In recent years, several immunodominant and putatively pathogen-specific membrane lipoproteins of *T. pallidum* have been identified in patients with syphilis and in infants with congenital syphilis. These patients and infants developed antigen specific antibodies which could be detected by immunoblot and by enzyme immunoassay. Therefore, recent methods of detection use recombinant antigens, mainly the membrane-integrated proteins 47 kDa, 17 kDa and 15 kDa (TP47, TP17, and TP15, respectively), in treponemal ELISA tests. Although TP47 was the earliest identified, as well as the most abundant and highly immunogenic [Norgard et al., Infect Immun 54:500-506 (1986)], the later identified TP15 and TP17, present in lower amounts, are also strongly immunogenic [Purcell et al., Infect Immun 57:3708-3714 (1989); Akins et al., Infect Immun 61:1202-1210 (1993)].

Given the increase in reported cases of syphilis and the periodic epidemics, as well as the severity of the disease, a need continues to exist for sensitive and specific immunoassays for detection of *Treponema pallidum*.

BRIEF SUMMARY OF THE INVENTION

To this end, the invention provides a recombinant plasmid encoding a *Treponema pallidum* triplet antigen. The plasmid comprises nucleic acid encoding an amino acid sequence selected from the group consisting of SEQ ID NO:7, SEQ ID NO:8, SEQ ID NO:9, SEQ ID NO:10, SEQ ID NO:11, and SEQ ID NO:12.

The invention further provides a recombinant plasmid encoding a *Treponema pallidum* triplet antigen, the recombinant plasmid selected from the group consisting of: the plasmid designated p261nS-TP17-15-47 and deposited with the American Type Culture Collection ("ATCC") as ATCC Accession No. PTA-11590 on Jan. 12, 2011; the plasmid designated p261nS-TP47-17-15 and deposited with the American Type Culture Collection as ATCC Accession No. PTA-11589 on Jan. 12, 2011; the plasmid designated p261nS-TP17-47-15; the plasmid designated p261nS-TP47-15-17; the plasmid designated p261nS-TP15-17-47; and the plasmid designated p261nS-TP15-47-17.

Vectors, host cells, and triplet antigen production methods using the host cells are also provided.

Additionally, the invention provides the *Treponema pallidum* triplet antigen having an amino acid sequence selected from the group consisting of SEQ ID NO:7, SEQ ID NO:8, SEQ ID NO:9, SEQ ID NO:10, SEQ ID NO:11, and SEQ ID NO:12. A method of detecting the presence of *Treponema pallidum* antibodies in a sample is further provided, which uses the *Treponema pallidum* triplet antigen, as well as kits for such detection.

Additional features and advantages of the subject invention will be apparent from the description which follows when considered in conjunction with the attached figures.

DETAILED DESCRIPTION OF THE INVENTION

The assay (detection method) of the subject invention uses recombinant *Treponema pallidum* (TP) (the causative agent of Syphilis) outer membrane protein antigens to detect patient sample anti-IgG, anti-IgM, and anti-IgA antibodies. The recombinant protein antigens of interest are a 15 kilodalton antigen (TP15), a 17 kilodalton antigen (TP17), and a 47 kilodalton antigen (TP47). A fused recombinant antigen construct has been developed which incorporates the three antigens of interest as well as human copper zinc superoxide dismutase (hSOD). In addition to the *Treponema pallidum* antigenic sequences and the hSOD, δ 10 amino acid tag (the "261sequence") is present at the N-terminus of the fused antigen construct to facilitate evaluation by Western blot and ELISA, and to provide a means for affinity purification if desired. The assay of the subject invention uses this fused recombinant antigen construct.

Figure 1:
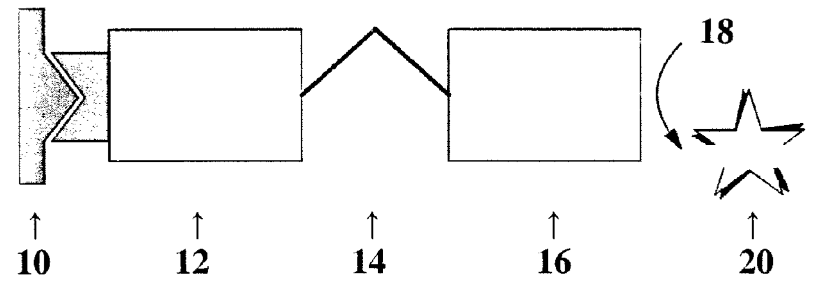
FIG. 1 illustrates the reaction scheme for the VITROS® Syphilis TPA test.
Figure 2:
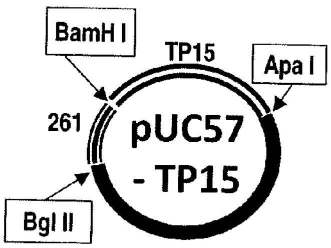
FIG. 2 shows the plasmid map of pUC57-TP15.
Figure 3:
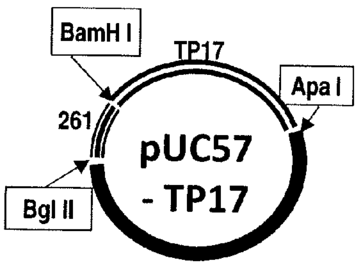
FIG. 3 shows the plasmid map of pUC57-TP17.
Figure 4:
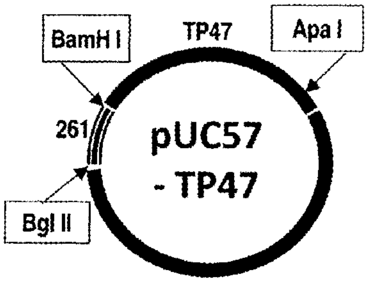
FIG. 4 shows the plasmid map of pUC57-TP47.
Figure 5:
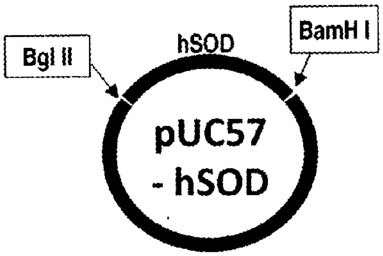
FIG. 5 shows the plasmid map of pUC57-hSOD.

In one embodiment, the assay is the VITROS® Syphilis TPA test and the assay is performed using the VITROS® ECi/ECiQ Immunodiagnostic Systems, VITROS® 3600 Immunodiagnostic System, or VITROS® 5600 Integrated System using Intellicheck® Technology. Each of these analyzers is available from Ortho-Clinical Diagnostics, Inc. (OCD), 100 Indigo Creek Drive, Rochester, N.Y. 14626. Throughout this application, the use of the trademark VITROS® refers to the line of chemistry and immunodiagnostic analyzers and products commercially available from OCD. The use of the trademark INTELLICHECK® refers to the technology commercially available from OCD which monitors, verifies, and documents diagnostic checks throughout sample and assay processing for accurate and efficient result reporting. An immunometric immunoassay technique is used, which involves the reaction of IgG, IgM or IgA antibodies present in the sample with a biotinylated recombinant TP antigen and a horseradish peroxidase (HRP)-labeled recombinant TP antigen conjugate. The antibody-antigen complex is captured by streptavidin on the wells (SAC wells). Unbound materials are removed by washing. The bound HRP conjugate is measured by a luminescent reaction. A reagent containing luminogenic substrate (a luminol derivative and a peracid salt) and an electron transfer agent is added to the wells. The HRP in the bound conjugate catalyzes the oxidation of the luminol derivative, producing light. The electron transfer agent (a substituted acetanilide) increases the level of light produced and prolongs its emission. The light signals are read by the analyzer system. The bound HRP conjugate is directly proportional to the concentration of anti-TP antibody present. This reaction scheme is illustrated in FIG. 1, where 10 represents the streptavidin coasted well, 12 represents the biotinylated TP antigen, 14 represents the antibodies to TP antigens present in a sample, 16 represents HRP labeled TP antigen, 18 represents signal reagent with enhancer, and 20 represents luminescence. Superoxide dismutase is present in the assay biotin reagent formulation to block binding of anti-SOD antibodies that may be present in the patient sample. This prevents a false reactive signal from being generated.

The invention provides a recombinant plasmid encoding a *Treponema pallidum* triplet antigen. The plasmid comprises nucleic acid encoding an amino acid sequence selected from the group consisting of SEQ ID NO:7, SEQ ID NO:8, SEQ ID NO:9, SEQ ID NO:10, SEQ ID NO:11, and SEQ ID NO:12.

In one embodiment, the plasmid is designated p261nS-TP17-15-47 and is deposited with the American Type Culture Collection ("ATCC") as ATCC Accession No. PTA-11590. Plasmid p261nS-TP17-15-47 includes nucleic acid having the nucleotide sequence as shown in SEQ ID NO:3, encoding the triplet antigen construct having the amino acid sequence as shown in SEQ ID NO:9. In this particular embodiment, amino acids 5-14 encode the 261 tag, amino acids 17-150 encode TP17, amino acids 155-277 encode TP15, amino acids 282-695 encode TP47, and amino acids 697-849 encode hSOD.

In another embodiment, the plasmid is designated p261nS-TP47-17-15 and is deposited with the American Type Culture Collection as ATCC Accession No. PTA-11589. Plasmid p261nS-TP47-17-15 includes nucleic acid having the nucleotide sequence as shown in SEQ ID NO:6, encoding the triplet antigen construct having the amino acid sequence as shown in SEQ ID NO:12. In this particular embodiment, amino acids 5-14 encode the 261 tag, amino acids 17-430 encode TP47, amino acids 435-568 encode TP17, amino acids 573-695 encode TP15, and amino acids 697-849 encode hSOD.

In a further embodiment, the plasmid is designated p261nS-TP17-47-15. Plasmid p261nS-TP17-47-15 includes nucleic acid having the nucleotide sequence as shown in SEQ ID NO:4, encoding the triplet antigen construct having the amino acid sequence as shown in SEQ ID NO:10. In this particular embodiment, amino acids 5-14 encode the 261 tag, amino acids 17-150 encode TP17, amino acids 155-568 encode TP47, amino acids 571-693 encode TP15, and amino acids 695-847 encode hSOD.

In yet another embodiment, the plasmid is designated p261nS-TP47-15-17. Plasmid p261nS-TP47-15-17 includes nucleic acid having the nucleotide sequence as shown in SEQ ID NO:5, encoding the triplet antigen construct having the amino acid sequence as shown in SEQ ID NO:11. In this particular embodiment, amino acids 5-14 encode the 261 tag, amino acids 17-430 encode TP47, amino acids 435-557 encode TP15, amino acids 560-693 encode TP17, and amino acids 695-847 encode hSOD.

In an additional embodiment, the plasmid is designated p261nS-TP15-17-47. Plasmid p261nS-TP15-17-47 includes nucleic acid having the nucleotide sequence as shown in SEQ ID NO:1, encoding the triplet antigen construct having the amino acid sequence as shown in SEQ ID NO:7. In this particular embodiment, amino acids 5-14 encode the 261 tag, amino acids 17-139 encode TP15, amino acids 143-276 encode TP17, amino acids 281-694 encode TP47, and amino acids 696-848 encode hSOD.

In another additional embodiment, the plasmid is designated p261nS-TP15-47-17. Plasmid p261nS-TP15-47-17 includes nucleic acid having the nucleotide sequence as shown in SEQ ID NO:2, encoding the triplet antigen construct having the amino acid sequence as shown in SEQ ID NO:8. In this particular embodiment, amino acids 5-14 encode the 261 tag, amino acids 17-139 encode TP15, amino acids 143-556 encode TP47, amino acids 559-692 encode TP17, and amino acids 694-846 encode hSOD.

The ATCC is located at 10801 University Boulevard, Manassas, Va. 20110-2209 USA, and each of the above deposits was made on Jan. 12, 2011 under the Budapest Treaty on the International Recognition of the Deposit of Microorganisms for the Purposes of Patent Procedure (the "Budapest Treaty").

Each *Treponema pallidum* triplet antigen construct includes three *Treponema pallidum* antigens (TP15, TP17, and TP47). While each has been defined by its amino acid sequence as well as a nucleotide sequence, it should be readily apparent that nucleotide additions, deletions, and/or substitutions, such as those which do not affect the translation of the DNA molecule, are within the scope of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting triplet (i.e. its ability to detect anti-TP15, anti-TP17, and/or anti-TP47 antibodies).

Amino acid additions, deletions, and/or substitutions which do not negate the ability of the resulting triplet to detect anti-TP15, anti-TP17, and/or anti-TP47 antibodies are thus within the scope of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson [J Molecular Evolution 19:171-175 (1983)], Taylor [J Theor Biol 119:205-218 (1986)], and Bordo and Argos [J Mol Biol 217:721-729 (1991)].

While the presently preferred vector system for provision of the nucleic acid encoding the triplet antigen construct is a plasmid vector, other vector systems can also be used. Furthermore, while the presently preferred host cell for expression of the triplet antigen construct is the bacterial host cell *Escherichia coli*, any suitable host and/or vector system can be used to express the triplet antigen construct. Other suitable bacterial hosts, yeasts hosts (such as *Saccharomyces cerevisiae*), as well as mammalian (for example, Hela cells, Cv-1 cells, COS cells) and insect hosts (such as *Drosophila* cell lines), can be used.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into the suitable host cells. For example, DNA encoding the triplet antigen can be injected into the nucleus of a host cell or transformed into the host cell using a suitable vector, or mRNA encoding the triplet antigen can be injected directly into the host cell, in order to obtain expression of triplet antigen in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller [Bioessays 11:91-95 (1989)]. Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. [Molecular Cloning: A Laboratory Manual, 2d Edition, Cold Spring Harbor Laboratory Press, Cold Spring Harbor, N.Y. (1989)].

Host cells into which the nucleic acid encoding the triplet antigen has been introduced can be used to produce (i.e. to functionally express) the triplet antigen.

The subject invention further provides a *Treponema pallidum* triplet antigen having an amino acid sequence selected from the group consisting of SEQ ID NO:7, SEQ ID NO:8, SEQ ID NO:9, SEQ ID NO:10, SEQ ID NO:11, and SEQ ID NO:12. Presently preferred embodiments of the triplet antigen are those represented by SEQ ID NO:9 and SEQ ID NO:12. These embodiments present the TP17 portion of the triplet before the TP15 portion of the triplet, and higher antibody detection sensitivity is achieved with these constructs. All constructs include a leader sequence (presently preferred is a ten amino acid leader sequence (tag 261), though other suitable leaders could be substituted). All constructs further include human copper zinc superoxide dismutase (hSOD), a low immunogenic protein, at the carboxy terminus. Eleven lysine residues in the hSOD provide sites for biotin attachment and HRP conjugation, and two cystein residues are mutated to serine (Cys 4 and Cys 112) to prevent interchain protein polymerization [Hallewel et al., J Biol Chem 264: 5260-5268 (1989)]. This construct is thus optimized for in vitro diagnosis of syphilis infection. Other suitable low immunogenic proteins which provide similar sites for biotin attachment and HRP conjugation could be substituted. In the presently preferred plasmid construction, the triplet antigen is under the control of the T5 promoter.

While the specific details of an assay for detecting the presence of *Treponema pallidum* antibodies in a sample are disclosed below, generally the method comprises: contacting a sample with the *Treponema pallidum* triplet antigen of the subject invention, wherein *Treponema pallidum* antibodies present in the sample bind to the *Treponema pallidum* triplet antigen forming an antibody/antigen complex; and detecting the antibody/antigen complex, thereby detecting the presence of the *Treponema pallidum* antibodies. For use in an assay format for the detection of antibodies to *Treponema pallidum*, the antigen triplet may be labeled with a detectable marker. Suitable markers include, for example, enzymatic labels such as horseradish peroxidase or alkaline phosphatase, as well as fluorescent labels (such as fluorescein, rhodamine, and green fluorescent protein).

The assay format may also utilize biotin/avidin/streptavidin in the provision of the triplet antigen bound to a solid phase. Suitable solid phases include, for example, any non-aqueous matrix to which the triplet antigen can be bound. Such solid phases are well known in the immunoassay arts, and include, for example, polystyrene plates, polyacrylamides, glass, polysaccharides, polyvinyl alcohol and silicones. Microslides, microwells, and microtips are all used as solid phases in immunoassays.

The assay format may involve direct detection of the antibody/antigen complex (see FIG. 18), which can comprise: contacting the antibody/antigen complex with a second *Treponema pallidum* triplet antigen of the subject invention, wherein the second *Treponema pallidum* triplet antigen is labeled with a detectable marker (HRP as shown). The second *Treponema pallidum* triplet antigen binds to the antibody present in the antibody/antigen complex forming an antigen/antibody/labeled antigen complex, which is then detected thereby detecting the presence of *Treponema pallidum* antibodies in the sample.

The assay format may involve indirect detection of the antibody/antigen complex (see FIG. 19), which can comprise: contacting the antibody/antigen complex with labeled anti-human antibody (monoclonal mouse anti-human antibody as shown). The labeled anti-human antibody binds to the antibody present in the antibody/antigen complex forming an antigen/antibody/labeled anti-antibody complex, which is then detected thereby detecting the presence of *Treponema pallidum* antibodies in the sample.

For all assays of the subject invention, the sample can be any suitable sample (for example, serum, plasma, and EDTA or heparin plasma) but is preferably a serum sample.

The *Treponema pallidum* triplet antigen construct of the subject invention can thus be utilized as a component of a kit for detection of *Treponema pallidum* antibodies. A kit is provided which comprises the *Treponema pallidum* triplet antigen construct, and additionally a second *Treponema pallidum* triplet antigen construct labeled with a detectable marker (an "enzyme conjugate" such as HRP-labeled *Treponema pallidum* triplet antigen) (see above discussion of markers). The kit can also comprise suitable positive and/or negative controls, calibration samples, enzyme conjugates, substrate for enzyme conjugates (such as O-phenylenediamine), buffer solution, and washing solution.

The details of the construction of the triplet antigen and its use in an assay for detection of *Treponema pallidum* antibodies in a patient sample are described below.

Synthetic Genes.

*T. pallidum* outer membrane protein genes TP15, TP17, and TP47 were each synthesized based on amino acid sequence P16055 (amino acid 19-141), P29722 (amino acid 23-156) and P29723 (amino acid 21-434), respectively, published in the central database UniProt (http://www.uniprot.org). Human copper zinc superoxide dismutase (hSOD) gene was synthesized based on amino acid sequence P00441 (amino acid 2-154), except two Cystein residues (amino acid 7 and 112) were mutated to Serine to prevent polymerization. All four synthesized gene codons were optimized for bacterial expression and each was inserted at the EcoR V site on host plasmid pUC57. The resulting plasmids, pUC57-15, pUC57-17, pUC57-45, and pUC57-hSOD, are shown in FIGS. 2-5, respectively.

The four synthetic genes do not bear stop codons and any internal Apa I, BamH I, Bgl II, EcoR I and Hind III sites that were used in subsequent subcloning described below. Restriction enzyme sites, with or without tag gene (261 sequence), were incorporated into the four synthetic genes.

Expression Vector and TP Doublet Construction.

Figure 6:
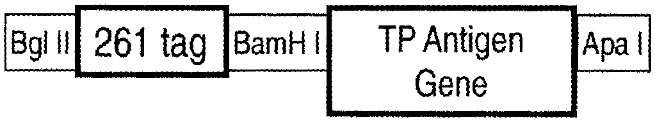
FIG. 6 shows the TP construct for cloning into pB10G.
Figure 8:
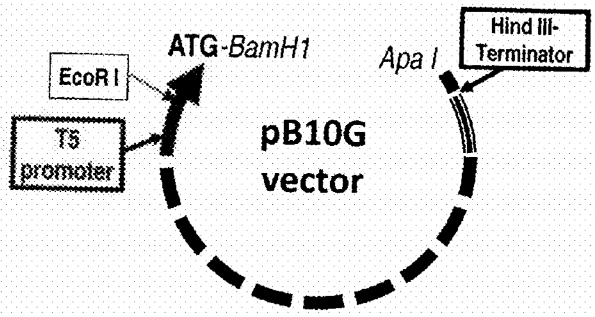
FIG. 8 shows the plasmid map of pB10G.
Figure 9:
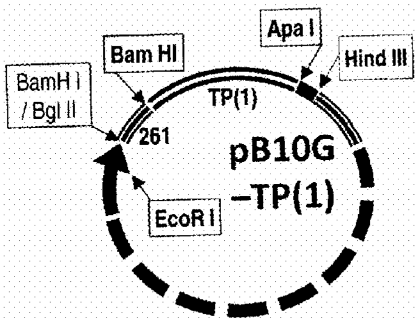
FIG. 9 shows the plasmid map of pB10G-TP(1)
Figure 10:
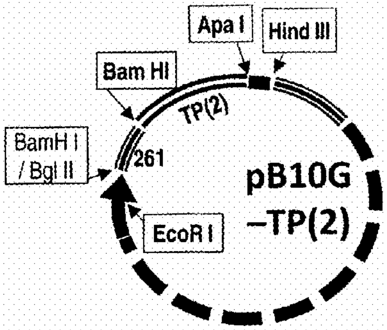
FIG. 10 shows the plasmid map of pB10G-TP(2)
Figure 11:
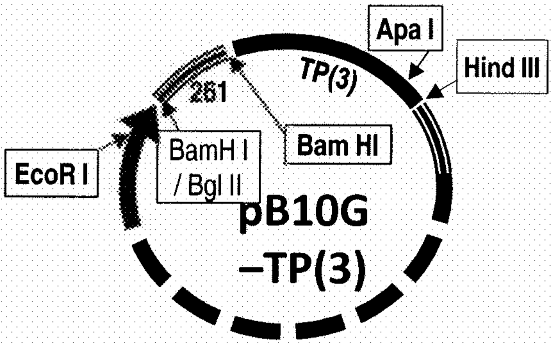
FIG. 11 shows the plasmid map of pB10G-TP(3)
Figure 12:
FIG. 12 shows the TP(1) construct for cloning into pB10G-TP(2)
Figure 13:
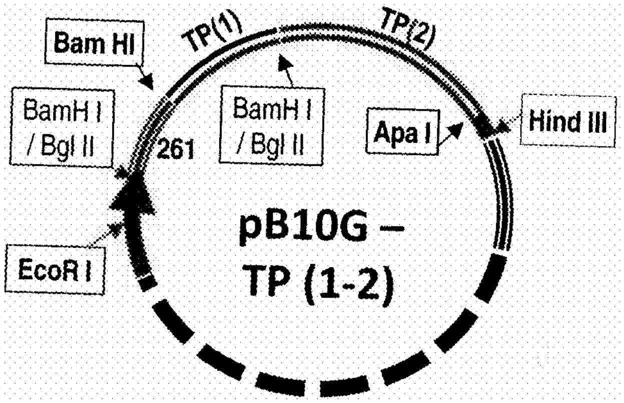
FIG. 13 shows the plasmid map of pB10G-TP(1-2)
Figure 14:
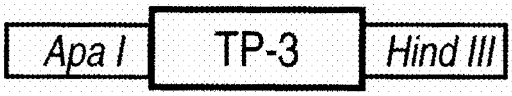
FIG. 14 shows the TP(3) construct for cloning into pB10G-TP(1-2)

Each of the TP genes from pUC57 was digested by Bgl II and Apa I (see FIG. 6 for resulting TP construct) and separately cloned into BamH I and Apa I sites of a previously constructed expression vector, pB10G (see FIG. 8), which contained a T5 promoter, an ATG start site, and unique restriction sites EcoR I, BamH I, Apa I and Hind III. This generated three expressional vectors, pB10G-TP15, pB10G-TP17 and pB10G-TP47 (shown generically as pB10G-TP(1), pB10G-TP(2), and pB10G-TP(3) in FIGS. 9-11, respectively). Ligation of the compatible Bgl II ends of the gene fragments and the BamH I ends on the plasmids eliminated the Bgl II/BamH I restriction enzyme sites in all three constructs. The TP doublet was created by subcloning. To construct a TP doublet subclone (see FIG. 13), a DNA gene insert was produced by PCR reaction using the second antigen expression vector as template and a pair of forward and reverse primers. The forward primer covered the EcoR I site, located in the T5 promoter region, upstream of the TP gene. The reverse primer matched the end of the TP gene and converted the Apa I site to a Bgl II site. This PCR product was then digested with EcoR I/Bgl II (see FIG. 12 for resulting TP-1 construct) and cloned into another antigen expression vector which was cut open with EcoR I and BamH I. Likewise, ligation of the compatible Bgl II on the insert and the BamH I on the host eliminated both restriction enzyme sites.

TP Triplet Construction.

To produce six final triplet fusion genes, four TP doublet vectors, pB10G-TP17-TP47, pB10G-TP15-TP47, pB10G-TP47-TP15 and pB10G-TP17-TP15, were used as the host and the third TP gene was either added at the 5' end of the TP doublet or added at the 3' end of the TP doublet. The TP(1-2) double vector is shown generically in FIG. 13 and the TP(3) construct for insertion into the doublet vector is shown in FIG.

Figure 15:
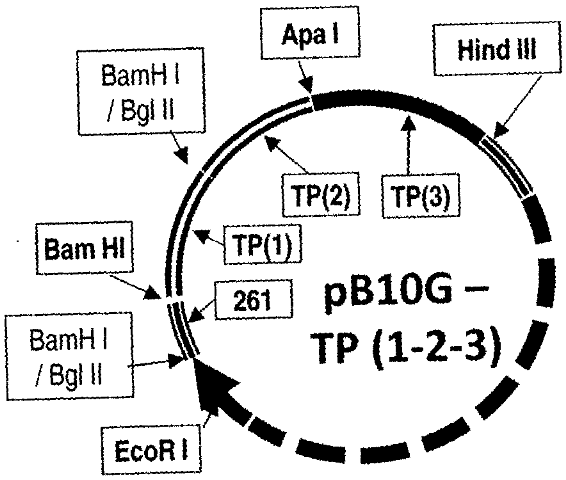
FIG. 15 shows the plasmid map of pB10G-TP(1-2-3)

14. To add the insert at the 3' end, a DNA gene insert was produced by PCR reaction using the third antigen expression vector as template and a pair of forward and reverse primers. The forward primer matched the 5' end of TP gene and contained a Apa I site. The reverse primer matched the 3' end of TP gene and contained a Hind III site. This PCR product was then digested with Apa I/Hind III and cloned into the doublet expression vector which was cut open with the appropriate restriction enzymes. Triplets pB10G-TP15-TP17-TP47, pB10G-TP17-TP15-TP47 and pB10G-TP47-TP17-TP15 were made by adding the third TP gene at the doublet 5' end, while triplets pB10G-TP15-TP47-TP17, pB10G-TP47-TP15-TP17 and pB10G-TP17-TP47-TP15 were made by adding the third TP gene at the doublet 3' end. PCR primers used in creating the doublets and triplets are listed in Table 4, PCR Primers, Group A. This triplet construct is shown generically in FIG. 15.

TP Triplet with SOD Fusion Construction.

Figure 7:
FIG. 7 shows the hSOD construct for cloning into a pB10G triplet plasmid.
Figure 16:
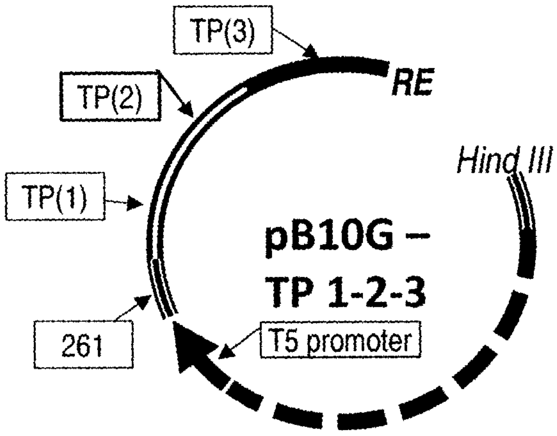
FIG. 16 shows the plasmid map of pB10G-TP(1-2-3) with the unique restriction enzyme site.
Figure 17:
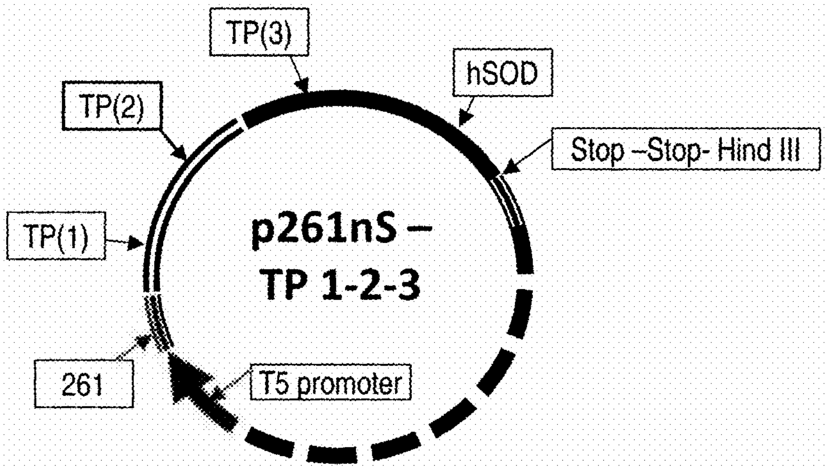
FIG. 17 shows the plasmid map of p261nS-TP(1-2-3)

The TP triplet with a C-terminal SOD fusion tag (shown generically in FIG. 17) was created through "two-round" PCR and cloning. "Two-round PCR" was performed to link the C-terminal TP3 with SOD (see FIG. 7 for SOD construct) and to introduce restriction enzyme sites for cloning. The first round of PCR was composed of two separate PCR reactions, with the reverse primer (Table 4, PCR Primers, Group B) in one PCR reaction complementing the forward primer (Table 4, PCR Primers, Group C) in the other PCR reaction. In the second round of PCR, the two products from the first round PCR were combined and amplified with a third set of nested primers (Table 4, PCR Primers, Group D). The forward primer matched the TP3 sequence and contained a unique restriction enzyme (RE) site. The reverse primer matched the 3' end SOD. Two stop codons and a Hind III site created a new DNA insert (see FIG. 16). To fuse the SOD gene to the existing *T. pallidum* triplet, the new PCR product was digested and directly cloned into a pB10G-TP triplet plasmid digested at the designed unique restriction site and the Hind III site to yield pB10G-TP(1-2-3)-SOD (see FIG. 17). As used herein, TP1, TP2, and TP3 represent the three *T. pallidum* antigens, TP15, TP17, and TP47, in any order. Thus, TP1 could be TP15, TP2 could be TP17, and TP3 could be TP47. Other combinations include: TP1 could be TP15, TP2 could be TP47, and TP3 could be TP17; TP1 could be TP17, TP2 could be TP15, and TP3 could be TP47; TP1 could be TP17, TP2 could be TP47, and TP3 could be TP15; TP1 could be TP47, TP2 could be TP15, and TP3 could be TP17; and TP1 could be TP47, TP2 could be TP17, and TP3 could be TP15.

All PCR amplifications were performed with Taq polymerase using a standard sequence of 35 PCR cycles: 95° C. (15 sec), 55° C. (20 sec), 72° C. (30 sec). Nucleotide sequences of the PCR primers are listed in Table 4. Usage of each primer in creating particular triplets is indicated. All PCR products were purified following a Qiagen PCR kit protocol. All restriction enzymes were purchased from New England Biolabs. Plasmids were prepared using Qiagen DNA Miniprep kits. All six triplet coding regions were DNA sequenced (SEQ ID NOs:1-6) and amino acid sequences translated (SEQ ID NOs:7-12).

The assay of the subject invention provides for the measurement of antibodies to three *T. pallidum* antigens, TP15, TP17 and TP47. The assay is performed on antigen precoated microtiter plates. Samples are added to the microtiter plate wells and incubated. *T. pallidum* IgG/IgM specific antibodies, if present, will bind to and become immobilized by the antigen pre-coated on the wells. The bound antibodies were detected either in a direct conjugated antigen sandwich format (see FIG. 18), or in an indirect format detected by conjugated anti-human IgG and IgM (see FIG. 19).

More particularly, recombinant TP triplets were coated passively on an ELISA high-binding plate well surface as capture antigen. The plate was then blocked with 1% BSA/PBS to cover all unbound well surfaces. Syphilis infected patient's serum or plasma was added in wells and incubated for a first incubation period, enabling *T. pallidum* antibody (IgG, IgM, and IgA) in the sample to react with the precoated triplet antigens. Unbound materials were washed away after the first incubation. For the direct assay, HRP conjugated recombinant TP triplet was the detector and was added into the wells and incubated for a second incubation period. After the second incubation, unbound triplet conjugates were washed away. The formed antigen-human *T. pallidum* antibody (IgG/IgM)-antigen complex was measured by adding peroxidase substrate solution, then the reaction was stopped after 30 minutes and optical density was recorded for analysis. For the indirect assay, an HRP conjugated mouse monoclonal anti-human IgG and HRP conjugated mouse monoclonal anti-human IgM mixture was the detector and was added into the wells and incubated for the second incubation period. After the second incubation, unbound conjugates were washed away. The formed anti-human IgG/IgM-human *T. pallidum* antibody (IgG/IgM)-antigen complex was measured by adding peroxidase substrate solution, then the reaction was stopped after 30 minutes and optical density was recorded for analysis.

The engineered recombinant *T. pallidum* triplet has a 10 amino acid leader sequence (tag 261) at the N-terminus and two to four amino acid linkers between each TP antigen. The tag 261 sequence was derived from human placenta growth factor (P1GF). The human copper zinc superoxide dismutase (hSOD) is incorporated at the C-terminus of the *T. pallidum* antigen triplet to form a fusion protein.

hSOD has been used previously in various recombinant antigen fusions in diagnostic assays for infectious pathogens such as HCV, HIV etc. hSOD is a small size, low immunogenic human endogenous protein, which has 153 amino acids with a molecular weight of about 16 kD. The 11 lysine residues in hSOD provide extra conjugation site for biotinylation and HRP conjugation.

EXAMPLE I

ELISA Assay Reagents, Format, and Protocol

Assay Reagents:

96 well microtiter high-binding plate (Costar)

Coating buffer (10 mM phosphate, 2 mM EDTA, pH 7.0), blocking buffer (1% BSA in PBS, pH 7.0), washing solution (PBS with 0.05% tween-20), sample buffer (Blocker Casein in PBS with 0.05% tween-20, Pierce)

ELISA specimen and conjugate diluent: Blocker Casein in PBS from Pierce. Tween 20 was added to a final of 0.05% before use. In the direct assay, hSOD lysate was added together with HRP conjugated TP triplet.

Purified recombinant TP triplet fusions, their sequences were validated by DNA sequencing (see SEQ ID NOs: 1-6). Proteins were expressed in prokaryotic *E. coli* cell. Protein purity was validated to be greater than 87% by SDS PAGE.

HRP (horseradish peroxidase) conjugated recombinant TP triplet.

150 ng/mL, Phosphate, pH=7.2, Molarity=50 mM

HRP conjugate reagent buffer contains: H2O, K2HPO4 (anhydrous), KH2PO4 (anhydrous), NaCl, BSA liquid, KFeCN, ANS, Tween-20, Anti-foam 204, ProClin 950

HRP (horseradish peroxidase) conjugated mouse monoclonal anti-261 tag

HRP (horseradish peroxidase) conjugated mouse monoclonal anti-human IgG

HRP (horseradish peroxidase) conjugated mouse monoclonal anti-human IgM

HRP (horseradish peroxidase) substrate tablet (O-Phenylenediamine-2HCl) and solution and stop solution are components from Ortho-Clinical Diagnostics general ELISA products.

Specimens: Syphilis Positive plasma, Syphilis Negative plasma, SeraCare Syphilis mixed titer panel (PS C202) and Zeptometrix Syphilis mixed titer panel (K-ZMC002)

Figure 18:
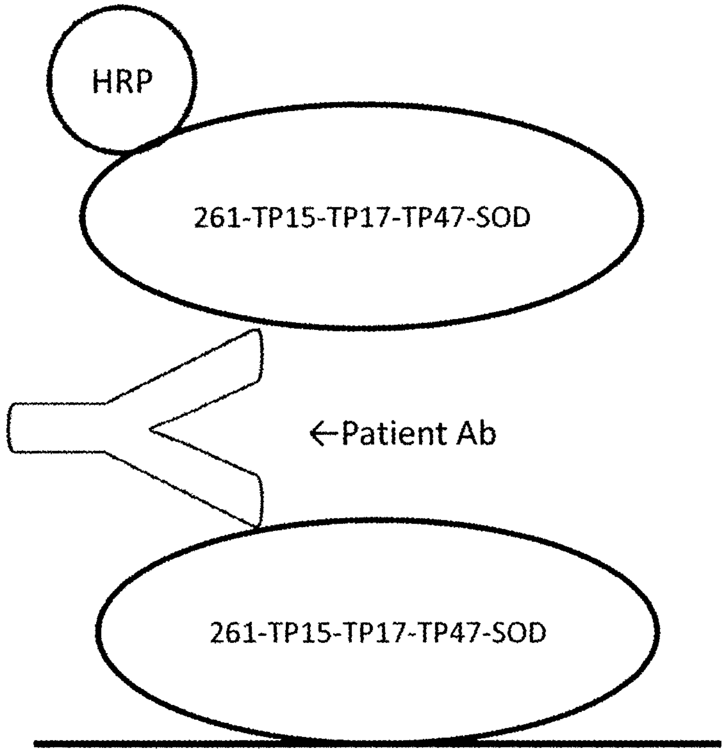
FIG. 18 illustrates the direct assay format according to the subject invention.
Figure 19:
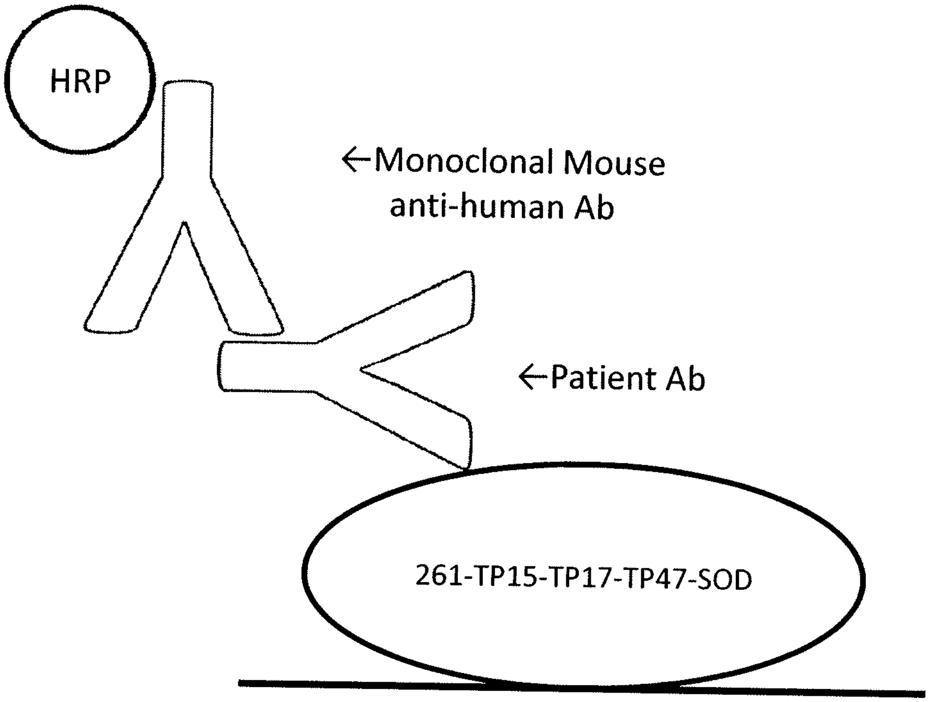
FIG. 19 illustrates the indirect assay format according to the subject invention.

The ELISA Assay Format is shown in FIGS. 18 and 19, both a direct assay format and an indirect assay format.

ELISA Assay Protocol:

Plate coating: 1) add 100 uL/well coating solution containing 2 ug/mL of TP triplet fusion at 25° C. for 18 hrs. 2) Wells were washed once with washing buffer and 290 uL/well blocking buffer were added for 1 hr/25° C. blocking 3) After blocking buffer aspirated, plates were dried greater than 4 hrs in a low humidity incubator. 4) Plate was pouched in an air-proof sealed bag until use.

Direct Assay Protocol:

Assay: 1) Add 50 uL Casein (PBS) specimen diluent and 50 uL specimen (or control) to each well. Plate was incubated for 30 min at 37° C. with shaking 2) After 6 times wash with washing solution; add 100 uL HRP conjugated TP triplet fusion diluted in Casein (PBS) to each well. Plate was incubated for 30 min at 37° C. with shaking 3) After 6 times wash, add 100 uL OPD substrate and incubate in dark for 30 min at 25° C. 4) Add 25 uL stop solution and read optical density (OD) at 492 nm.

Indirect Assay Protocol:

Assay: 1) Add 90 uL Casein (PBS) specimen diluent and 10 uL specimen (or control) to each well. Plate was incubated for 15 min at 37° C. with shaking 2) After 6 times wash with washing solution; add 100 uL HRP conjugate mixture containing HRP-mouse monoclonal anti-human IgG and HRP-mouse monoclonal anti-human IgM diluted in casein (PBS) to each well. Plate was incubated for 15 min at 37° C. with shaking 3) After 6 times wash, add 100 uL OPD substrate and incubate in dark for 30 min at 25° C. 4) Add 25 uL stop solution and read optical density (OD) at 492 nm.

EXAMPLE II

Evaluation of Triplet Constructs

ELISA Reaction:

(1) Wells were coated with a serial dilution of six TP triplets and post-coated with 1% BSA in PBS. (2) Add 100 uL HRP conjugated mouse monoclonal anti-261 tag diluted in Casein (PBS) to antigen precoated wells, and incubate at 37° C. for 15 minutes with shaking (2) Wash 6 times, add 100 uL OPD substrate solution, and incubate at RT for 15 min in dark. (4) Add 25 uL 4N sulfuric acid stop solution and read at 490 nm.

Results shown in Table 1 were ODs. Proposed TP Triplet coating concentrations were derived from calculation to calibrate antigen quantity immobilized on the plate and used in plate coating in the antibody assay evaluation.

ELISA Reaction:

(1) Wells were coated with six TP triplets at a concentration defined in Table-1, and post-coated with 1% BSA in PBS. (2) Add 50 ul Casein (PBS) and 50 ul panel specimens to antigen precoated wells, and incubate at 37° C. for 15 minutes with shaking (3) Wash 6 times, add 100 ul HRP conjugated TP triplet antigens, and incubate at 37° C. for 15 minutes with shaking HRP conjugated antigen is the antigen coated on the plates. (4) Wash 6 times, add 100 uL OPD substrate solution, and incubate at RT for 15 min in dark. (4) Add 25 uL 4N sulfuric acid stop solution and read at 490 nm.

Results shown in Table 2 were S/C values. S is OD signal, C is cut-off, equals 5 times of an average OD given by three negative controls.

ELISA Reaction:

(1) Add 90 ul Casein and 10 ul panel sample (2 fold serial diluted in normal human plasma) to antigen precoated wells, and incubate at 37° C. for 15 minutes with shaking (2) Wash 6 times, add 100 ul conjugate mixture containing HRP mouse monoclonal anti-human IgG and monoclonal anti-human IgM, and incubate at 37° C. for 15 minutes with shaking (3) Wash 6 times, add 100 uL OPD substrate solution, and incubate at RT for 15 minutes in dark. (4) Add 25 uL 4N sulfuric acid stop solution and read at 490 nm.

Results shown in Table 3 were final dilution of ZeptoMetrix panel specimen with normal human plasma (1:X, X==), at which dilution the specimens were determined to be positive (signal over cut-off >1). The cut-off is 5 times of an average OD given by three negative controls.

EXAMPLE III

Details of VITROS® Syphilis TPA Test

The principles of the VITROS® Syphilis TPA test using the TP15-TP17-TP47 triplet construct are as described above and as shown in FIG. 1. A kit is provided which includes a reagent pack and a calibrator. The reagent pack contains: 100 coated wells (streptavidin, bacterial; binds ≥2 ng biotin/well); 13.1 mL biotinylated antigen reagent (biotin-recombinant TP antigens 0.15 ug/mL) in buffer with bovine gamma globulin, bovine serum albumin, and antimicrobial agent; and 20.4 mL conjugate reagent (HRP-recombinant TP antigens, 0.15 ug/mL) in buffer with bovine serum albumin and antimicrobial agent). The calibrator contains VITROS® Syphilis TPA Calibrator (human syphilis IgG positive plasma, 2.2 mL) with antimicrobial agent. The test uses 25 uL of calibrator for each determination.

Suitable specimens for use with the test are serum, heparin plasma, EDTA plasma, and citrate plasma. The test uses 25 uL of sample (specimen) for each determination.

The test also uses signal reagent (such as VITROS® Immunodiagnostic Products Signal Reagent), wash reagent (such as VITROS® Immunodiagnostic Products Universal Wash Reagent), and quality control materials (such as VITROS® Immunodiagnostic Products Syphilis TPA Controls).

The test uses a 16-minute first incubation period, and an 8-minute second incubation period, with a time for first result of 34 minutes. The test is performed at 37° C.

Results are automatically calculated by the VITROS® Immunodiagnostic and VITROS® Integrated Systems, and represent "signal for test sample"/"signal at cutoff (cutoff value)". Samples with results of <0.80 will be flagged as "negative", samples with results ≥0.80 and <1.20 will be flagged as "borderline", and samples with results ≥1.20 will be flagged as "reactive". Negative indicates no active or previous infection with *Treponema pallidum*; borderline indicates the test is unable to determine if *Treponema pallidum* infection has occurred, and the sample should be re-tested; and reactive indicates active or previous infection with *Treponema pallidum.*

EXAMPLE IV

Performance Characteristics of the VITROS® Syphilis TPA Test

Referring to Table 5, initial sensitivity and specificity was assessed on a population of 4290 samples using the VITROS® Syphilis TPA test and a commercially available immunoassay ("IA 1") for antibodies to *Treponema pallidum*. An initial analysis in the VITROS® Syphilis TPA test gave an initial specificity, including borderline samples (4015/4016) of 99.98% (exact 95% Cl 99.9-100.0%). Initial sensitivity, including borderline samples (266/274) was 97.08% (exact 95% Cl 194.3-98.7%). One (0.025%) sample was borderline in the VITROS® Syphilis TPA test. The commercially available test did not have a borderline region.

Referring to Table 6, relative specificity and sensitivity after resolution of uninterpretable samples was assessed. This included samples where there was a difference in classification from the commercial test (reactive/negative) (defined as "discordant"). Samples that resulted in discordant or borderline results (either in the VITROS® or IA 1 test) were further tested to determine relative sensitivity and specificity. A total of 9 discordant and borderline samples were further tested by first repeating the VITROS® Syphilis TPA test in duplicate. A total of 9 discordant and borderline samples remained discordant with IA 1 after repeat testing in the VITROS® Syphilis TPA test. The 9 samples were also tested in up to 4 additional commercially available assays for antibodies to *Treponema pallidum*. The median VITROS® Syphilis TPA result was then compared to the consensus classification of the other 4 commercially available tests. Using this algorithm, 8 samples were resolved as syphilis antibody negative and one sample remained borderline in the VITROS® Syphilis TPA test. After resolution of discordant results, the relative specificity of the VITROS® Syphilis TPA test to the IA 1 test was calculated (4023/4024) as 99.98% (exact Cl 99.9-100.0%) and relative sensitivity (266/266) as 100% (exact Cl 98.6-100.0%).

Referring to Table 7, 149 samples containing potentially cross-reacting sub-groups were tested in the VITROS® Syphilis TPA test and in a commercially available test (EIA 1). The sub-groups included: HAV IgG and IgM, HBV IgG and IgM, HCV IgG and IgM, EBV IgG and IgM, anti-HSV IgG and IgM, anti-HIV 1/2 IgG and IgM, CMV IgG and IgM, Rubella IgG and IgM, ANA/SLE, *Borrelia burgdorferi* infection (European and US strain), *Toxoplasma gondii* infections IgG and IgM, heterophilic antibodies/HAMA and Rheumatoid factor. The specificity (137/137) was 100.0% (95% Cl 97.3-100.0%) and sensitivity (12/12) was 100.0% (95% Cl 73.5%-100.0%). No discordant samples were observed and all results were in line with the expected clinical performance in the commercially available test. Thus, none of the samples was found to cross react with the VITROS® Syphilis TPA assay to cause any mis-classification of results.

Precision on the VITROS® ECi/ECiQ Immunodiagnostic System was evaluated. Two replicates each of 4 patient sample pools and 4 control samples were tested on 2 separate occasions per day on at least 20 different days. The experiment was performed using 2 reagent lots on two different systems. Precision on the VITROS® 3600 Immunodiagnostic System and the VITROS® 5600 Integrated System was also evaluated. Two replicates each of 4 patient sample pools and 4 control samples were tested on 2 separate occasions per day on at least 20 different days. The experiment was performed using 1 reagent lot on each system. Results showed precision for samples at the cut off up to strong positives averaged 1.6% (range 0.9-3.2%) within run, 4.8% (range 2.7-9.0%) within calibration, and 4.6% (range 2.1-9.0%) within lab. The VITROS® Syphilis TPA test thus gives excellent precision across the borderline and reactive ranges, on all VITROS® systems.

Referring to Table 8, the VITROS® Syphilis TPA test was evaluated for interference. Of the compounds tested, none was found to interference with the clinical interpretation of the test at the concentration indicated.

The VITROS® Syphilis TPA test was also evaluated with two sets of proficiency samples from CAP and NEQAS and two commercially available performance panels (Zeptometrix and BBI-Seracare). 100% agreement was obtained with these proficiency samples and performance panels.

Samples types were also evaluation on the VITROS® Syphilis TPA test. Five normal donor samples were collected as serum (SST, clot activator and on the clot glass tubes), as heparin plasma (lithium and sodium), EDTA plasma and citrate plasma. From five other donors, 50 mL of whole blood was collected. This was spiked with a syphilis reactive plasma and dispensed into the same type of tubes as mentioned above to mimic syphilis reactive donors. Bias between sample type was assessed. No large differences were observed between sample types compared to serum. For citrate samples, the recovery compared to serum was lower due to the dilutional effect of the citrate. A stability study using these samples demonstrated that samples can be stored for 7 days at 2-8° C. and 4 weeks at −20° C. without significant loss of dose results or change in clinical classification.

Taking all performance characteristics into account, the VITROS® Syphilis TPA test combines good analytical and clinical performance with the operational simplicity of a rapid automated continuous random access immunoassay.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

TABLE 1

Calibration Coated Six TP Triplet Antigens on Plate

| Plate coated TP | OD signal probed by HRP anti-261 (2 ng/mL) | | | | | | Proposed TP Triplet coating |
|---|---|---|---|---|---|---|---|
| Triplet [ug/ml] | 4.00 | 2.00 | 1.00 | 0.50 | 0.25 | 0.13 | [ug/mL] |
| TP15-17-47-SOD | over | 3.006 | 2.372 | 1.490 | 0.914 | 0.613 | 1.00 |
| TP15-47-17-SOD | over | 2.916 | 2.106 | 1.356 | 0.843 | 0.566 | 1.20 |
| TP17-15-47-SOD | over | 3.144 | 3.193 | 2.508 | 1.494 | 0.891 | 0.50 |
| TP17-47-15-SOD | over | 1.454 | 0.914 | 0.580 | 0.346 | 0.263 | 2.80 |
| TP47-15-17-SOD | over | 3.310 | 2.481 | 1.950 | 1.209 | 0.713 | 0.65 |
| TP47-17-15-SOD | over | 3.523 | 3.626 | 3.489 | 2.434 | 1.426 | 0.25 |

TABLE 2

Evaluation of Syphilis Reactive Specimens by Direct ELISA

| Plate: TP Triplet Coated | | SeraCare Syphilis mixed titer panel (PS C202) -- (S/C Values) | | | | | | | | | |
|---|---|---|---|---|---|---|---|---|---|---|---|
| ID | [ug/ml] | #1 | #2 | #3 | #4 | #5 | #6 | #7 | #8 | #9 | #10 |
| TP15-17-47-SOD | 1.00 | 3.0 | 5.4 | 1.1 | 0.0 | 2.6 | 2.6 | 8.0 | 1.3 | 7.7 | 4.0 |
| TP15-47-17-SOD | 1.20 | 4.5 | 7.2 | 2.7 | 0.0 | 1.8 | 4.5 | 14 | 4.0 | 7.8 | 6.1 |
| TP17-15-47-SOD | 0.50 | 4.9 | 10 | 3.4 | 0.0 | 3.0 | 4.9 | 15 | 6.7 | 15 | 6.7 |
| TP17-47-15-SOD | 2.80 | 3.1 | 8.8 | 3.0 | 0.0 | 2.6 | 4.9 | 4.7 | 5.6 | 15 | 6.7 |
| TP47-15-17-SOD | 0.65 | 4.4 | 9.7 | 1.9 | 0.0 | 3.1 | 4.9 | 17 | 3.4 | 15 | 5.4 |
| TP47-17-15-SOD | 0.25 | 4.9 | 10 | 3.3 | 0.0 | 4.2 | 4.9 | 15 | 6.0 | 15 | 6.7 |
| Plate: TP Triplet Coated | | | | | | | | | | | |
| ID | [ug/ml] | #11 | #12 | #13 | #14 | #15 | #16 | #17 | #18 | #19 | #20 |
| TP15-17-47-SOD | 1.00 | 2.1 | 3.3 | 3.2 | 2.9 | 5.3 | 0.0 | 3.1 | 2.6 | 2.8 | 3.9 |
| TP15-47-17-SOD | 1.20 | 3.0 | 6.1 | 6.9 | 8.1 | 6.9 | 0.0 | 3.2 | 7.0 | 4.0 | 2.8 |
| TP17-15-47-SOD | 0.50 | 6.3 | 6.7 | 11 | 7.5 | 10 | 0.0 | 4.6 | 16 | 4.5 | 10 |
| TP17-47-15-SOD | 2.80 | 5.6 | 4.0 | 14 | 6.2 | 10 | 0.0 | 3.6 | 10 | 4.2 | 5.3 |
| TP47-15-17-SOD | 0.65 | 4.9 | 6.1 | 11 | 6.6 | 10 | 0.0 | 2.5 | 5.0 | 5.8 | 5.6 |
| TP47-17-15-SOD | 0.25 | 7.0 | 6.7 | 11 | 9.7 | 13 | 0.0 | 3.5 | 12 | 3.9 | 9.0 |

TABLE 3

Evaluation of Plate Coating Antigen Sequence Combination

| Plate: TP Triplet Coated | | ZeptoMetrix Mixed Titer Syphilis Panel (K-ZMC002) | | | | | | | |
|---|---|---|---|---|---|---|---|---|---|
| ID | [ug/ml] | #1 | #2 | #3 | #4 | #5 | #6 | #7 | #8 |
| TP15-17-47-SOD | 1.00 | 2 | 2 | 2 | 4 | 8 | 8 | 8 | 2 |
| TP15-47-17-SOD | 1.20 | 4 | 2 | 2 | 8 | 4 | 16 | 8 | 2 |
| TP17-15-47-SOD | 0.50 | 16 | 4 | 2 | 256 | 32 | 64 | 256 | 8 |
| TP17-47-15-SOD | 2.80 | 8 | 2 | 2 | 32 | 4 | 8 | 64 | 2 |
| TP47-15-17-SOD | 0.65 | 16 | 2 | 4 | 64 | 32 | 16 | 256 | 8 |
| TP47-17-15-SOD | 0.25 | 32 | 4 | 4 | 256 | 16 | 64 | 256 | 8 |

TABLE 3-continued

Evaluation of Plate Coating Antigen Sequence Combination

| Plate: TP Triplet Coated | | | | | | | | |
|---|---|---|---|---|---|---|---|---|
| ID | [ug/ml] | #9 | #10 | #11 | #12 | #13 | #14 | #15 |
| TP15-17-47-SOD | 1.00 | 2 | 32 | 2 | 2 | 4 | 256 | 8 |
| TP15-47-17-SOD | 1.20 | 2 | 16 | 2 | 2 | 4 | 32 | 8 |
| TP17-15-47-SOD | 0.50 | 32 | 256 | 8 | 64 | 32 | 256 | 32 |
| TP17-47-15-SOD | 2.80 | 2 | 256 | 2 | 8 | 8 | 256 | 16 |
| TP47-15-17-SOD | 0.65 | 16 | 256 | 4 | 16 | 16 | 256 | 32 |
| TP47-17-15-SOD | 0.25 | 16 | 256 | 8 | 32 | 16 | 256 | 64 |

TABLE 4

PCR Primers

| | | | Primers used in creating triplet of | | | | | | |
|---|---|---|---|---|---|---|---|---|---|
| Group | Name | Primer Direction | 15-17-47 | 17-15-47 | 15-47-17 | 47-15-17 | 17-47-15 | 47-17-15 | Comments |
| A | F4-ER | Forward | yes | yes | yes | yes | yes | yes | EcoR I, vector sequence |
| | Apa-TP15 | Forward | | | | | yes | | Apa -(TP15) . . . |
| | Apa-TP17 | Forward | | | yes | yes | | | Apa -(TP17). . . |
| | TP15-BG | Reverse | | yes | | | | | . . . TP15-gly-pro-Bgl II |
| | TP15-BG2 | Reverse | yes | | yes | | | | . . . TP15-gly-Bgl II |
| | TP17-BG | Reverse | yes | yes | | | yes | yes | . . . TP17-gly-pro-Bgl II |
| | TP47-BG2 | Reverse | | | | yes | | yes | . . . TP47-gly-pro-Bgl II |
| B | F-15 | Forward | | | | | yes | yes | 50 bp before SacI in TP15 |
| | R-15S | Reverse | | | | | yes | yes | TP15(3')-SOD(5') |
| | T17-BH | Forward | | | yes | yes | | | 95 bp before Eag I in TP17 |
| | R-17S | Reverse | | | yes | yes | | | TP17(3')-SOD(5') |
| | F-47b | Forward | yes | yes | | | | | 50 bp before Xma in TP47 |
| | R-47S | Reverse | yes | yes | | | | | TP47(3')-SOD(5') |
| C | F-15S | Forward | | | | | yes | yes | TP15(3')-SOD(5') |
| | F-17S | Forward | | | yes | yes | | | TP17(3')-SOD(5') |
| | F-47S | Forward | yes | yes | | | | | TP47(3')-SOD(5') |

TABLE 4-continued

PCR Primers

| | | | | | | | | | |
|---|---|---|---|---|---|---|---|---|---|
| | RS | Reverse | yes | yes | yes | yes | yes | yes | downstream of SOD gene |
| D | T15-Sac | Forward | | | | | yes | yes | (TP15) . . . SacI . . . |
| | TP17-EAG | Forward | | | yes | yes | | | (TP17) . . . EagI . . . |
| | T47-XMA | Forward | yes | yes | | | | | (TP47) . . . Xma1 . . . |
| | RS-H3 | Reverse | yes | yes | yes | yes | yes | yes | SOD(3')-StopStop-Hind III |

| Group | Name | Primer Sequence (5'-3') |
|---|---|---|
| A | F4-ER | SEQ ID NO: 13: cacaGAATTCATTAAAGAGGAGAAATTAAC |
| | Apa-TP15 | SEQ ID NO: 14: tgtctGGGCCCAGCTTTTCTAGTATTCCGA |
| | Apa-TP17 | SEQ ID NO: 15: tgtctGGGCCCGTGAGCTGCACCACGGT |
| | TP15-BG | SEQ ID NO: 16: agctggAGATCTCGGGCCGCGAGAGATAATGGCTTCTT |
| | TP15-BG2 | SEQ ID NO: 17: gctggAGATCTACCGCGAGAGATAATGGCTTCTT |
| | TP17-BG | SEQ ID NO: 18: agctggAGATCTCGGGCCTTTCTTGGTTTTCTTCAGAACGTA |
| | TP47-BG2 | SEQ ID NO: 19: agctggAGATCTTGGACCCTGCGCCACCACTTTCGCG |
| B | F-15 | SEQ ID NO: 20: CGCGACCGTGAGCTCTCAGAGTTTT |
| | R-15S | SEQ ID NO: 21: CAGCACGCTGACGGCTTTGGTCGCgagGCGAGAGATAATGGCTTCTTTTTCGCC |
| | T17-BH | SEQ ID NO: 22: GTGAGCTGCACCACGGT |
| | R-17S | SEQ ID NO: 23: CAGCACGCTGACGGCTTTGGTCGCgagTTTCTTGGTTTTCTTCAGAACGTAAA |
| | F-47b | SEQ ID NO: 24: GGTTAGCGATCAGGCCGT |
| | R-47S | SEQ ID NO: 25: CAGCACGCTGACGGCTTTGGTCGCgagCTGCGCCACCACTTTCGCGCGC |
| C | F-15S | SEQ ID NO: 26: GGCGAAAAAGAAGCCATTATCTCTCGCctcGCGACCAAAGCCGTCAGCGTGCTG |
| | F-17S | SEQ ID NO: 27: TTTACGTTCTGAAGAAAACCAAGAAActcGCGACCAAAGCCGTCAGCGTGCTG |
| | F-47S | SEQ ID NO: 28: GCGCGCGAAAGTGGTGGCGCAGctcGCGACCAAAGCCGTCAGCGTGCTG |
| | RS | SEQ ID NO: 29: TGCAGTCGACGGGCCCGGGAT |
| D | T15-Sac | SEQ ID NO: 30: CGCGACCGTGAGCTCTCAGAGTTTT |
| | TP17-EAG | SEQ ID NO: 31: CCCTGCCGGCCGCAGATTGT |
| | T47-XMA | SEQ ID NO: 32: GGATTTCACCCCGGGTACCGAATATA |
| | RS-H3 | SEQ ID NO: 33: agccAAGCTTcattaCTGGGCGATACCAATAACGCCA |

TABLE 5

VITROS Syphilis TPA Test

| | | Reactive | Borderline | Negative | Total |
|---|---|---|---|---|---|
| IA 1 | Reactive | 266 | 0 | 8 | 274 |
| | Negative | 0 | 1 | 4015 | 4016 |
| | Totals | 266 | 1 | 4023 | 4290 |

TABLE 6

VITROS Syphilis TPA Test

| | | Reactive | Borderline | Negative | Total |
|---|---|---|---|---|---|
| IA 1 | Reactive | 266 | 0 | 0 | 266 |
| | Negative | 0 | 1 | 4023 | 4024 |
| | Totals | 266 | 1 | 4023 | 4290 |

TABLE 7

VITROS Syphilis TPA Test

| | | Reactive | Borderline | Negative | Total |
|---|---|---|---|---|---|
| EIA 1 | Reactive | 12 | 0 | 0 | 12 |
| | Negative | 0 | 0 | 137 | 137 |
| | Totals | 12 | 0 | 137 | 149 |

TABLE 8

| Compound | Concentration | |
|---|---|---|
| Azide (sodium) | 20 mg/dL | 3.06 mmol/L |
| Bilirubin | 20 mg/dL | 0.342 mmol/L |
| Biotin | 1000 ng/dL | 40.8 nmol/L |
| BSA (High Protein) | 5 g/dL (total ~12 g/dL) | N/A |
| Cholesterol | 250 mg/dL | N/A |
| Hemoglobin (hemolysate) | 500 mg/dL | 0.155 mmol/L |
| Intralipid | 850 mg/dL | N/A |
| Triolein | 3000 mg/dL | 33.96 mmol/L |

The invention claimed is:

1. A *Treponema pallidum* triplet antigen with a sequence consisting of the amino acid sequence of SEQ ID NO:9.

2. The *Treponema pallidum* triplet antigen of claim 1 labeled with a detectable marker.

3. The *Treponema pallidum* triplet antigen of claim 2 wherein the detectable marker is horseradish peroxidase.

4. A method of detecting the presence of *Treponema pallidum* antibodies in a sample, the method comprising:

contacting the sample with the *Treponema pallidum* triplet antigen of claim 1, wherein *Treponema pallidum* antibodies present in the sample bind to the *Treponema pallidum* triplet antigen forming an antibody/antigen complex; and detecting the antibody/antigen complex, thereby detecting the presence of *Treponema pallidum* antibodies.

5. The method of claim 4 wherein the *Treponema pallidum* triplet antigen is immobilized on a solid support.

6. The method of claim 4 wherein detecting the antibody/antigen complex comprises: contacting the antibody/antigen complex with a second *Treponema pallidum* triplet antigen, wherein the second *Treponema pallidum* triplet antigen is the *Treponema pallidum* triplet antigen of claim 1 labeled with a detectable marker and wherein the second *Treponema pallidum* triplet antigen binds to the antibody present in the antibody/antigen complex forming an antigen/antibody/labeled antigen complex; and detecting the antigen/antibody/labeled antigen complex, thereby detecting the presence of *Treponema pallidum* antibodies.

7. The method of claim 4 wherein detecting the antibody/antigen complex comprises:

contacting the antibody/antigen complex with labeled anti-human antibody, wherein the labeled anti-human antibody binds to the antibody present in the antibody/antigen complex forming an antigen/antibody/labeled anti-antibody complex; and detecting the antigen/antibody/labeled anti-antibody complex, thereby detecting the presence of *Treponema pallidum* antibodies.

8. A component of a kit for detection of *Treponema pallidum* antibodies, the component comprising the *Treponema pallidum* triplet antigen of claim 1.

* * * * *

UNITED STATES PATENT AND TRADEMARK OFFICE

CERTIFICATE OF CORRECTION

PATENT NO. : 8,691,950 B2
APPLICATION NO. : 13/350235
DATED : April 8, 2014
INVENTOR(S) : Jian Zheng et al.

It is certified that error appears in the above-identified patent and that said Letters Patent is hereby corrected as shown below:

On the Title page

Item (73) Assignee
Change “Orth-Clinical Diagnostics, Inc.” to -- Ortho-Clinical Diagnostics, Inc. --.

Signed and Sealed this
Eighteenth Day of August, 2015

Michelle K. Lee
*Director of the United States Patent and Trademark Office*